US008563693B2

(12) United States Patent
Geiben-Lynn

(10) Patent No.: US 8,563,693 B2
(45) Date of Patent: Oct. 22, 2013

(54) METHOD OF TREATING HUMAN IMMUNODEFICIENCY VIRUS INFECTION IN A MAMMAL COMPRISING ADMINISTERING HEPARIN-ACTIVATED ANTITHROMBIN III

(75) Inventor: Ralf Geiben-Lynn, Watertown, MA (US)

(73) Assignee: Acceleration Biopharmaceuticals, Inc., Dover, DE (US)

( * ) Notice: Subject to any disclaimer, the term of this patent is extended or adjusted under 35 U.S.C. 154(b) by 617 days.

(21) Appl. No.: 12/727,853

(22) Filed: Mar. 19, 2010

(65) Prior Publication Data

US 2010/0255078 A1 Oct. 7, 2010

Related U.S. Application Data

(63) Continuation-in-part of application No. 12/391,669, filed on Feb. 24, 2009, now abandoned, which is a continuation-in-part of application No. 10/892,676, filed on Jul. 15, 2004, now Pat. No. 7,510,828, which is a continuation of application No. 10/057,593, filed on Jan. 25, 2002, now abandoned.

(60) Provisional application No. 60/264,338, filed on Jan. 26, 2001.

(51) Int. Cl.

| | |
|---|---|
| ***A61K 35/14*** | (2006.01) |
| ***A61K 9/127*** | (2006.01) |
| ***A61K 39/21*** | (2006.01) |
| ***C12Q 1/70*** | (2006.01) |

(52) U.S. Cl.

USPC ............. 530/381; 424/450; 424/208.1; 435/5

(58) Field of Classification Search

None

See application file for complete search history.

(56) References Cited

U.S. PATENT DOCUMENTS

| | | | | |
|---|---|---|---|---|
| 3,842,061 A | | 10/1974 | Andersson et al. | 260/112 |
| 4,340,589 A | | 7/1982 | Uemura et al. | 424/94.63 |
| 4,689,323 A | * | 8/1987 | Mitra et al. | 514/56 |
| 5,532,215 A | | 7/1996 | Lezdey et al. | 514/8 |
| 5,610,286 A | | 3/1997 | Shau et al. | 536/23.5 |
| 7,498,130 B2 | * | 3/2009 | Elmaleh | 435/5 |

FOREIGN PATENT DOCUMENTS

| | | |
|---|---|---|
| EP | 0090505 | 7/1982 |
| EP | 0339919 | 11/1989 |
| WO | WO 96/10638 | 4/1996 |
| WO | WO 96/39424 | 12/1996 |
| WO | WO 00/52034 | 9/2000 |

OTHER PUBLICATIONS

Whitney, J. B., et al., 2011, Serpin induced antiviral activity of prostaglandin synthetase-2 against HIV-1 replication, PLoS ONE 6(4):e18589(1-9).*

Geiben-Lynn, R., et al., 2002, Purification of a modified form of bovine antithrombin III as an HIV-1 CD8+ T-cell antiviral factor, J. Biol. Chem. 277(44):42352-42357.*

Levy, J. A., 2003, The search for the CD8+ cell anti-HIV factor (CAF), TRENDS Immunol. 24(12):628-632.*

Gait, M. J., and J. Karn, 1995, Progress in anti-HIV structure-based drug design, TIBTECH 13:430-438.*

Pope, M., and A. T. Haase, Jul. 2003, Transmission, acute HIV-1 infection and the quest for strategies to prevent infection, Nat. Med. 9(7):847-852.*

Letvin, N. L., and B. D. Walker, Jul. 2003, Immunopathogenesis and immunotherapy in AIDS virus infections, Nat. Med. 9(7):861-866.*

International Search Report for PCT/US02/02309, mailed on Aug. 7, 2002.

Supplementary European Search Report, mailed Feb. 11, 2004.

Antithrombin Deficiency, University of Illinois Urbana/Champaign, http://www.med.uiuc.edu/hematology/PDF%20Files/Antithrombin.pdf, last updated Jun. 26, 2001.

McKenna. Antithrombin Deficiency, http://www.emedicine.com/med/topic150.htm, last updated Sep. 3, 2003.

* cited by examiner

*Primary Examiner* — Jeffrey S. Parkin

(74) *Attorney, Agent, or Firm* — Burns & Levinson LLP; Janine M. Susan

(57) ABSTRACT

The invention includes a heparin activated Antithrombin III encapsulated into a sterically stabilized anti-HLA-DR immunoliposome for the treatment of HIV infection in a human patient.

5 Claims, 17 Drawing Sheets

| Serpin | Abbreviation[i] | Role[ii] | Primary function/target | Reference | Species[iii] |
|---|---|---|---|---|---|
| $\alpha_1$-Antichymotrypsin | ACT | In | chymotrypsin | a | M |
| $\alpha_1$-Antitrypsin | AAT | In | elastase | b | M/Am |
| $\alpha_2$-Antiplasmin | A2AP | In | plasmin | c | M |
| *Accessory gland protein* | *Acp76A* | O | *reproductive system* | d | *dme* |
| Angiotensinogen | ANGT | O | non-inhibitory, hormone precursor | e,f | M |
| Antithrombin | ANT | In/O | thrombin, factor Xa, anti-angiogenesis | g,h | M/F |
| Blood fluke serpins | Ac | N | inhibitory RCL, target unknown. *Schistosoma haematobium* major antigen | i | *sma/ja/ha* |
| Bomapin | Bomapin | In | inhibitory activity vs serine proteinases | j | *hsa* |
| *Bombyx mori* serpins | Ac | In, N | inhibitory activity vs serine proteinases | k | *bmo* |
| CI inhibitor | CI-I | In | complement CI esterase | l | M |
| Corticosteroid-binding globulin | CBG | O | non-inhibitory, hormone binding | m | M/Am |
| Factor Xa-directed anticoagulant | Ac | In | reversible noncovalent factor Xa inhibition | n | *aae* |
| Glia-derived nexin | GDN | O/In | neurite outgrowth, thrombin | o | M |
| Heat shock protein 47 | HSP47 | O | chaperone, folding, collagen processing | p | M/F |
| Heparin cofactor II | HEPII | In | thrombin/chymotrypsin | q,r | M/Am |
| Kallistatin | KAL | In | tissue kallikrein | s | M |
| Limulus intracellular coagulation inhibitor | LICI | In | factor C, limulus clotting enzyme, other serine proteases | t | *ttr* |
| *Manduca sexta* alaserpin (12 splie variants) | SERP-I | In, N | some show inhibitory activity vs serine *proteinases* | u | *mse* |
| Maspin | Maspin | In | tissue-type plasminogen activator/prevents metastasis | v,w | M |
| Monocyte/neutrophil elastase inhibitor | MNEI | In | proteinase 3, cathepsin G | x | M |
| Myeloid and erythroid nuclear-termination stage specific protein | MENT | O | chromatin condensation | y | *gga* |
| Nematode | Ac | N | many with inhibitory RCL, targets unknown | z | *cel* |
| Neuroserpin | NEUS | In | plasminogen activator, urokinase, plasmin | aa | M |
| Ovalbumin | OVAL | N | non-inhibitory | bb,cc | A |
| P16 | P16 | In | cathepsin G | dd | M |
| P18 | P18 | In | trypsin-like proteinases | ee,ff | *hsa* |
| PI9 | P19 | In | granzyme B | gg | M |
| Pigment epithelium-derived factor | PEDF | O | neurotrophic factor | hh | M |
| Plant serpins (e.g., protein Z) | Ac | In | inhibitory activity vs serine proteinase, target unknown | ii,jj | P |
| Plasminogen Activator Inhibitor-1 | PAI-1 | In | tissue-type plasminogen activator | kk | M |

Fig. 1A

| Plasminogen Activator Inhibitor-2 | PAI-2 | In | tissue-type plasminogen activator, intracellular signaling | ll;mm | M |
| --- | --- | --- | --- | --- | --- |
| Protein C Inhibitor | PCI | In | protein C | nn | M |
| Regeneration-Associated Protein | RASP-1 | In | liver regeneration, human homolog protein Z potent FXa inhibitor | oo | rno |
| Sea lamprey serpin | Ac | N | inhibitory RCL, target unknown | pp | pma |
| Signal crayfish | Ac | N | inhibitory RCL, target unknown | qq | ple |
| Squamous Cell Carcinoma Antigen-1 | SCCA-1 | In | inhibitory activity vs papain-like cysteine proteases | rr | hsa |
| Squamous Cell Carcinoma Antigen-2 | SCCA-2 | In | inhibitory activity vs serine proteinases | ss | M |
| Thyroxine-binding globulin | TBG | O | non-inhibitory, hormone binding | tt | M/Am |
| TP55 | Megsin | O | megakaryocyte maturation | uu | hsa |
| Uterine milk protein | UTMP | In/O | activin binding, inhibitory activity vs aspartic proteases | vv,ww | M |
| Viral serpin CmA | CmA | In | interleukin-converting enzyme 1β | xx | V |
| Ovine uterine serpine | OvUS | O | immunosuppressive properties | yy | |

[i] (Ac) Identified by its individual accession.

[ii] (In) Protease inhibitor; (O) other function; (N) not known.

[iii] Where sequences are present in more than one species, the class is given. (A) avian; (Am) amphibian; (F) fish; (M) mammalian; (P) plant; (V) viral. Italicized labels refer to individual species: *(aae) Aedes aegypti; (bmo) Bombyx mori; (cel) Caenorhabditis elegans; (dme) Drosophila melanogaster; (gga) Gallus gallus; (hsa) Homo sapiens; (mse) Manduca sexta; (ple) Pacifastacus leniusculus; (pma) Petromyzon marinus; (rno) Rattus norvegicus; (sma/ja/ha) Schistosoma mansoni, Schistosoma japonicum, Schistosoma haematobium; (ttr) Tachypleus tridentatus.*

[a]Kalsheker 1996 (review); [b]Patterson 1991 (review); [c]Holmes et al. 1987; [d]Wolfner et al. 1997; [e]Stein et al. 1989; [f]Arakawa et al. 1965; [g]O'Reilly et al. 1999; [h]Lane et al. 1992 (review); [i]Blanton et al. 1994; [j]Riewald and Schleef 1995; [k]Sasaki 1991; [l]Zeerleder et al. 1999 (review); [m]Pemberton et al. 1988; [n]Stark and James 1998; [o]Zurn et al. 1988; [p]Nakai et al. 1992; [q]Tollefsen et al 1982; [r]Church et al. 1985; [s]Wang et al. 1989; [t]Miura et al. 1994; [u]Jiang and Kanost 1997; [v]Sheng et al. 1998; [w]Zou et a'L 1994; [x]Sugimori et al. 1995; [y]Grigoryev et al. 1992; [z]Whisstock et al. 1999; [aa]Krueger et al. 1997; [bb]Wright 1984; [cc]Stein et al. 1989; [dd]Scott et al. 1999a; [ee]Sprecher et al. 1995; [ff]Dahlen et al. 1998; [gg]Bird et al. 1998; [hh]Steele et al 1993; [ii]Lundgard and Svensson 1989; [jj]Rasmussen et al. 1996; [kk]Reilly et al. 1994 (review); [ll]Dickinson et al. 1998; [mm]Astedt et al. 1998 (review); [nn]Suzuki et al. 1983; [oo]New et al. 1996; [pp]Robson et al. 1998; [qq]Liang and Soderhall 1995; [rr]Schick et al. 1998; [ss]Schick et al. 1998; [tt]Pemberton et al. 1988; [uu]Tsujimoto et al. 1997; [vv]McFarlane et aL 1992; [ww]Mathialagan and Hansen 1996; [xx]Ray et al. 1992; [yy]Peltier et al. 2000.

Fig. 1B

HRSPVEDVCTAKPR DIPVNPMCIYR SSEKKATEGQGSEQKIPGATNR RVW
ELSKANSHFATAFYQHLADSK NNNDNIFLSPLSISTAFAMTK LGACNNTL
TQLMEVFKFDTISEKTSDQIHFFFAK LNCRLYRKANK SSELVSANR LFGD
KSITFNETYQDISEVVYGAK LQPLDFKGNAEQSR LTINQWISNKTEGRIT
DVIPPQAINEFTVLVLVNTIYFKGLWKSK FSPENTRKELFYK ADGESCSV
LMMYQESKFRYR RVAESTQVLELPFKGDD ITMVLILPKLEKTLAKVEQEL
TPDMLQEWLDELTETLLVVHMPR FRIEDSFSVKEQLQDMGLEDLFSPE KS
RLPGIVAEGRSDLYVSDAFHKAFLEVNEEGSEAAASTVISIAGR SLNSDR
VTFKANRPFLVLIR EVALNTIIFMGR VANPCVD (SEQ ID:1)

Fig. 2C

SEQUENCE LISTING

<160> NUMBER OF SEQ ID NOS: 1

<210> SEQ ID NO 1
<211> LENGTH: 433
<212> TYPE: PRT
<213> ORGANISM: Human immunodeficiency virus

<400> SEQUENCE: 1

His Arg Ser Pro Val Glu Asp Val Cys Thr Ala Lys Pro Arg Asp Ile
1 5 10 15

Pro Val Asn Pro Met Cys Ile Tyr Arg Ser Ser Glu Lys Lys Ala Thr

-continued

```
            20                  25                  30

Glu Gly Gln Gly Ser Glu Gln Lys Ile Pro Gly Ala Thr Asn Arg Arg
        35                  40                  45

Val Trp Glu Leu Ser Lys Ala Asn Ser His Phe Ala Thr Ala Phe Tyr
    50                  55                  60

Gln His Leu Ala Asp Ser Lys Asn Asn Asn Asp Asn Ile Phe Leu Ser
65                  70                  75                  80

Pro Leu Ser Ile Ser Thr Ala Phe Ala Met Thr Lys Leu Gly Ala Cys
                85                  90                  95

Asn Asn Thr Leu Thr Gln Leu Met Glu Val Phe Lys Phe Asp Thr Ile
            100                 105                 110

Ser Glu Lys Thr Ser Asp Gln Ile His Phe Phe Phe Ala Lys Leu Asn
        115                 120                 125

Cys Arg Leu Tyr Arg Lys Ala Asn Lys Ser Ser Glu Leu Val Ser Ala
    130                 135                 140

Asn Arg Leu Phe Gly Asp Lys Ser Ile Thr Phe Asn Glu Thr Tyr Gln
145                 150                 155                 160

Asp Ile Ser Glu Val Val Tyr Gly Ala Lys Leu Gln Pro Leu Asp Phe
                165                 170                 175

Lys Gly Asn Ala Glu Gln Ser Arg Leu Thr Ile Asn Gln Trp Ile Ser
            180                 185                 190

Asn Lys Thr Glu Gly Arg Ile Thr Asp Val Ile Pro Pro Gln Ala Ile
        195                 200                 205

Asn Glu Phe Thr Val Leu Val Leu Val Asn Thr Ile Tyr Phe Lys Gly
    210                 215                 220

Leu Trp Lys Ser Lys Phe Ser Pro Glu Asn Thr Arg Lys Glu Leu Phe
225                 230                 235                 240

Tyr Lys Ala Asp Gly Glu Ser Cys Ser Val Leu Met Met Tyr Gln Glu
                245                 250                 255

Ser Lys Phe Arg Tyr Arg Arg Val Ala Glu Ser Thr Gln Val Leu Glu
            260                 265                 270

Leu Pro Phe Lys Gly Asp Asp Ile Thr Met Val Leu Ile Leu Pro Lys
        275                 280                 285

Leu Glu Lys Thr Leu Ala Lys Val Glu Gln Glu Leu Thr Pro Asp Met
    290                 295                 300

Leu Gln Glu Trp Leu Asp Glu Leu Thr Glu Thr Leu Leu Val Val His
305                 310                 315                 320

Met Pro Arg Phe Arg Ile Glu Asp Ser Phe Ser Val Lys Glu Gln Leu
                325                 330                 335

Gln Asp Met Gly Leu Glu Asp Leu Phe Ser Pro Glu Lys Ser Arg Leu
            340                 345                 350

Pro Gly Ile Val Ala Glu Gly Arg Ser Asp Leu Tyr Val Ser Asp Ala
        355                 360                 365

Phe His Lys Ala Phe Leu Glu Val Asn Glu Glu Gly Ser Glu Ala Ala
    370                 375                 380

Ala Ser Thr Val Ile Ser Ile Ala Gly Arg Ser Leu Asn Ser Asp Arg
385                 390                 395                 400

Val Thr Phe Lys Ala Asn Arg Pro Phe Leu Val Leu Ile Arg Glu Val
                405                 410                 415

Ala Leu Asn Thr Ile Ile Phe Met Gly Arg Val Ala Asn Pro Cys Val
            420                 425                 430

Asp
```

METHOD OF TREATING HUMAN IMMUNODEFICIENCY VIRUS INFECTION IN A MAMMAL COMPRISING ADMINISTERING HEPARIN-ACTIVATED ANTITHROMBIN III

RELATED APPLICATIONS

This application is a continuation-in-part application of U.S. Ser. No. 12/391,669, filed Feb. 24, 2009, which is a continuation-in-part application of U.S. Ser. No. 10/892,676, filed Jul. 15, 2004, which is a continuation of U.S. Ser. No. 10/057,593, filed Jan. 25, 2002, which claims priority to U.S. Ser. No. 60/264,338, filed Jan. 26, 2001, all of which are incorporated herein by reference in their entireties.

STATEMENT REGARDING FEDERALLY SPONSORED RESEARCH OR DEVELOPMENT

This invention was made, in part, with Government support under grant numbers N01 AI30048, N01 AI30049 and AI067854 awarded by the National Institutes of Health. The Government has certain rights in the invention.

FIELD OF THE INVENTION

The present invention relates to a method of antiviral treatment using a serpin that inhibits serine protease and binds heparin.

BACKGROUND OF THE INVENTION

The human retrovirus, human immunodeficiency virus (HIV) causes Acquired Immunodeficiency Syndrome (AIDS), an incurable disease in which the body's immune system breaks down leaving the victim vulnerable to opportunistic infections, e.g., pneumonia, and certain cancers, e.g., Kaposi's Sarcoma. AIDS is major global health problem. The Joint United Nations Programme on HIV/AIDS (UNAIDS) estimates that there are now over 34 million people living with HIV or AIDS worldwide, some 28.1 million of those infected individuals reside in impoverished sub-Saharan Africa. In the United States, one out of every 250 people is infected with HIV or have AIDS. Since the beginning of the epidemic, AIDS has killed nearly 19 million people worldwide, including some 425,000 Americans. AIDS has replaced malaria and tuberculosis as the world's deadliest infectious disease among adults and is the fourth leading cause of death worldwide.

There is still no cure for AIDS. There is, however, an armamentarium of antiretroviral drugs that prevent HIV from reproducing and ravaging the body's immune system. One such class of drugs are the reverse transcriptase inhibitors, e.g., abacavir, delaviridine, didanosine, efavirenz, lamivudine, nevirapine, stavudine, zalcitabine, and zidovudine, which attack an HIV enzyme called reverse transcriptase. Another class of drugs is the protease inhibitors, e.g., amprenavir, indinavir, nelfinavir, ritonavir, and saquinavir, which inhibit HIV enzyme protease.

First introduced in 1995, these protease inhibitors are widely used for the treatment of HIV infection alone or in combination with other antiretroviral drugs. Today, approximately 215,000 of the estimated 350,000 patients receiving treatment for HIV infection in the United States take at least one protease inhibitor.

Highly active antiretroviral drug therapy (HAART) is a widely used anti-HIV therapy that entails triple-drug protease inhibitor-containing regimens that can completely suppress viral replication (Stephenson, JAMA, 277: 614-6 (1997)). The persistence of latent HIV in the body, however, has been underestimated. It is now recognized that there exists a reservoir of HIV in perhaps tens of thousands to a million long-lived resting "memory" T lymphocytes (CD4), in which the HIV genome is integrated into the cells own DNA (Stephenson, JAMA, 279: 641-2 (1998)). This pool of latently infected cells is likely established during primary infection.

Such combination therapy is often only partially effective, and it is unknown how much viral suppression is required to achieve durable virologic, immunologic, and clinical benefit (Deeks, JAMA, 286: 224-6 (2001)). Anti-HIV drugs are highly toxic and can cause serious side effects, including heart damage, kidney failure, and osteoporosis. Long-term use of protease inhibitors has been linked to peripheral wasting accompanied by abnormal deposits of body fat. Other manifestations of metabolic disruptions associated with protease inhibitors include increased levels of triglycerides and cholesterol, pancreatitis, atherosclerosis, and insulin resistance (Can et al., LANCET, 351: 1881-3 (1998)). The efficacy of current anti-HIV therapy is further limited by the complexity of regimens, pill burden, and drug-drug interactions. Compliance with the toxic effects of antiretroviral drugs make a lifetime of combination therapy a difficult prospect and many patients cannot tolerate long-term treatment with HAART. There is an urgent need for other antiviral therapies due to poor adherence to combination therapy regimes, which has led to the emergence of drug-resistant strains of HIV. Other drugs may improve compliance by substantially reducing the daily "pill burden" and simplifying the complicated dietary guidelines associated with the use of current protease inhibitors.

The HIV virus enters the body of an infected individual and lives and replicates primarily in the white blood cells. The hallmark of HIV infection, therefore, is a decrease in cells called T-helper or CD4 cells of the immune system. The molecular mechanism of HIV entry into cells involves specific interactions between the viral envelope glycoproteins (env) and two target cell proteins, CD4 and a chemokine receptor. HIV cell tropism is determined by the specificity of the env for a particular chemokine receptor (Steinberger et al., PROs. NATL. ACAD. ScI. USA. 97: 805-10 (2000)). T-cell-line-tropic (T-tropic) viruses (X4 viruses) require the chemokine receptor CXR4 for entry. Macrophage (M)-tropic viruses (R5 viruses) use CCR5 for entry (Berger et al., NATURE, 391: 240 (1998)). T-tropism is linked to various aspects of AIDS, including AIDS dementia, and may be important in disseminating the virus throughout the body and serving as a reservoir of virus in the body.

CD8+ T-cells secrete soluble factor(s) capable of inhibiting both R5- and X4-tropic strains of HIV and that are believed to play a critical role in vivo in antiviral host defense (Garizino-Demo et al., PROC. NATL. ACAD. SCI. USA, 96:111986-91 (1999)). These inhibitory factors include CC-chemokines (Cocchi et al., SCIENCE, 270: 1811-5 (1995); Horuk et al., J. BIOL. CHEM., 273: 386-91 (1998); Pal et al, SCIENCE, 278: 695-8 (1997)), that bind to the CCR5 coreceptor and inhibit R5 viral entry into cells (Garizino-Demo et al., PROC. NATL. ACAD. SCI. USA., 96: 111986-91 (1999); Liu et al., CELL, 86: 367-77 (1996); Samson et al., NATURE, 382: 722-5 (1996); Scarlatti et al., NAT. MED., 3: 1259-65 (1997)) as well as less well characterized soluble factor(s) produced by CD8+ T-cells and termed CD8+ T-cell antiviral factor(s) (hereinafter, CAF) capable of inhibiting both R5 and X4 HIV (Walker et al., SCIENCE, 234: 1563-6 (1986); Chen et al., AIDS REs. Hum RETROVIRUSES, 9:1079-86 (1993);

Mackewicz et al., PROC. NATL. ACAD. SCI. USA, 92:2308-12 (1995); Mackewicz et al., J. GEN. VIROL., 81 Pt.S: 1261-4 (2000); Leith et al., AIDS, 11: 575-80 (1997); Le Borgne et al., J. VIROL., 74: 4456-64 (2000); Tomaras et al., PROC. NATL. ACAD. SCI. USA, 97: 3503-8 (2000)). These CC-chemokines, however, do not account for all CAF antiviral activity released from these cells, particularly since CAF can inhibit the replication of X4 HIV strains that use CXCR4 and not CCR5 as a coreceptor. The identity of the factor(s) released from CD8+ T-cells capable of inhibiting X4 HIV has remained elusive.

SUMMARY OF THE INVENTION

The invention provides compositions comprising substantially purified serpin, which are useful in methods for the treatment and prevention of HIV infection. The invention also includes methods for the treatment and prevention of HIV infection comprising contacting a composition of the invention with a human patient or treating HIV infection by introducing into a cell susceptible to HIV infection a DNA molecule encoding a serpin. Additionally, the invention provides antibodies and kits useful in the detection, treatment, and prevention of HIV infection.

The present invention provides a method of inhibiting the infectivity of HIV by contacting an HIV virion with a composition comprising a substantially purified preparation of a serpin, or analog thereof. The composition is incubated with the virion for a period of time sufficient to inhibit the infectivity of HIV. The serpin may be selected from, but is not limited to, a group consisting of antithrombin (ATIII), protein C-inhibitor, activated protein C, plasminogen activator inhibitor, and alpha-1-antitrypsin A and may be pretreated chemically or enzymatically, e.g., elastase pretreatment. The serpin may be either bovine-originated or human-originated. In a preferred embodiment, the serpin, or analog thereof, inhibits serine protease and binds heparin. In a more preferred embodiment, a 43 kDa modified form of antithrombin III (hereinafter, mATIII) from activated CD8+ T-cell supernatants is used as an HIV inhibitory factor capable of inhibiting the replication of both R5 and X4 HIV. In a most preferred embodiment, the composition is comprised of 43 kDa ATIII (hereinafter mATIII), R-ATIII, S-ATIII, or a combination thereof.

The serpin composition may be used in a method of decreasing the infectivity of HIV, if any is present, in a biological sample by contacting the biological sample with an amount of serpin sufficient to decrease the infectivity of HIV in the biological sample. In a preferred embodiment, biological samples are contacted with serpin at a concentration of at least about 2 U/ml final biological sample volume. Biological samples which may treated for HIV infection include, but are not limited to, blood, plasma, serum, semen, cervical secretions, saliva, urine, breast milk, and amniotic fluids.

The present invention also provides a method of treating HIV infection by introducing a DNA molecule encoding a serpin into a cell susceptible to HIV infection, and expressing the serpin in an amount sufficient to inhibit infection of the cell by the HIV. Similarly, the present invention provides a method of treating HIV infection in a subject, the method comprising introducing into the subject a producer cell that expresses a serpin in an amount sufficient to inhibit infection of an endogenous cell of the subject, the endogenous cell being susceptible to HIV infection. In these methods, the expressed serpin preferably inhibits serine protease and binds heparin. In a preferred embodiment, the expressed serpin is ATIII, protein C-inhibitor, activated protein C, plasminogen activator inhibitor, or α-1-antitrypsin. In a more preferred embodiment, the expressed serpin is mATIII, R-ATIII, S-ATIII, or combination thereof.

The present invention further provides a purification system comprised of a serpin, or analog thereof, associated with a surface, wherein the serpin is capable of inhibiting the infectivity of HIV. A method of inhibiting the infectivity of HIV is provided by the present invention where an HIV virion is contacted with a composition having a surface that comprises substantially purified serpin associated with the surface for a length of time sufficient to inhibit the infectivity of HIV. In particular, the serpin may be associated with a bead, chip, column, or matrix. The present invention further provides a kit for detecting a protein that inhibits the infectivity of HIV. In particular, the kit comprises an antibody that specifically binds a serpin, or analog thereof. Also, the detection reagent contained in the kit is selected from the group consisting of an enzyme and a radionucleotide. In these methods, the expressed serpin preferably inhibits serine protease and binds heparin. In a preferred embodiment, the expressed serpin is ATIII, protein C-inhibitor, activated protein C, plasminogen activator inhibitor, or alpha-1-antitrypsin. In a more preferred embodiment, the expressed serpin is mATIII, R-ATIII, S-ATIII, or combination thereof.

The serpins of the invention can be used in a method of decreasing the infectivity of HSV (i.e. HSV-1 or HSV-2) or HCV in a biological sample containing cells susceptible to HSV infection by identifying a biological sample in which a decrease or elimination of HSV infectivity is desirable; and contacting the biological sample containing cells susceptible to HSV infection with an effective amount of S-antithrombin or an amount of S-antithrombin-bound-to-heparin, mATIII, R-ATIII, S-ATIII, or combination thereof. In a preferred embodiment, biological samples are contacted with serpin at a concentration of at least about 2 U/ml, 5 U/ml or 10 U/ml final biological sample volume. Biological samples which may treated for HIV infection include, but are not limited to, blood, plasma, serum, semen, cervical secretions, saliva, urine, breast milk, and amniotic fluids.

These and other objects of the present invention will be apparent from the detailed description of the invention provided below.

BRIEF DESCRIPTION OF THE DRAWINGS

The present invention will be further understood from the following description with reference to the figures in which:

FIG. 1 details members of the serpin protein superfamily. This table was modified from: Irving et al., GENOME RESEARCH 10: 1845-64 (2000).

FIGS. 2A-C detail the analytical data used to identify mATIII as a soluble HIV inhibitor secreted by $CD8^+$ T-cells. FIG. 2A is a C4 HPLC chromatogram of the substantially purified HIV inhibitor, mATIII. FIG.2B is a silver stained SDS-PAGE gel of the substantially purified HIV inhibitor, mATIII. FIG. 2C is a table of the partial protein sequence of HIV inhibitor (SEQ ID:1) obtained by in-gel trypsin digestion of the SDS PAGE HIV inhibitor protein band, elution of the resultant HIV-derived inhibitor peptides and nano-electrospray tandem mass spectrometry.

FIG. 4 is a graph comparing the effect of different forms of ATIII on X4 HIV, SIV, and SHIV infectivity.

DETAILED DESCRIPTION OF THE INVENTION

Figure 2A:
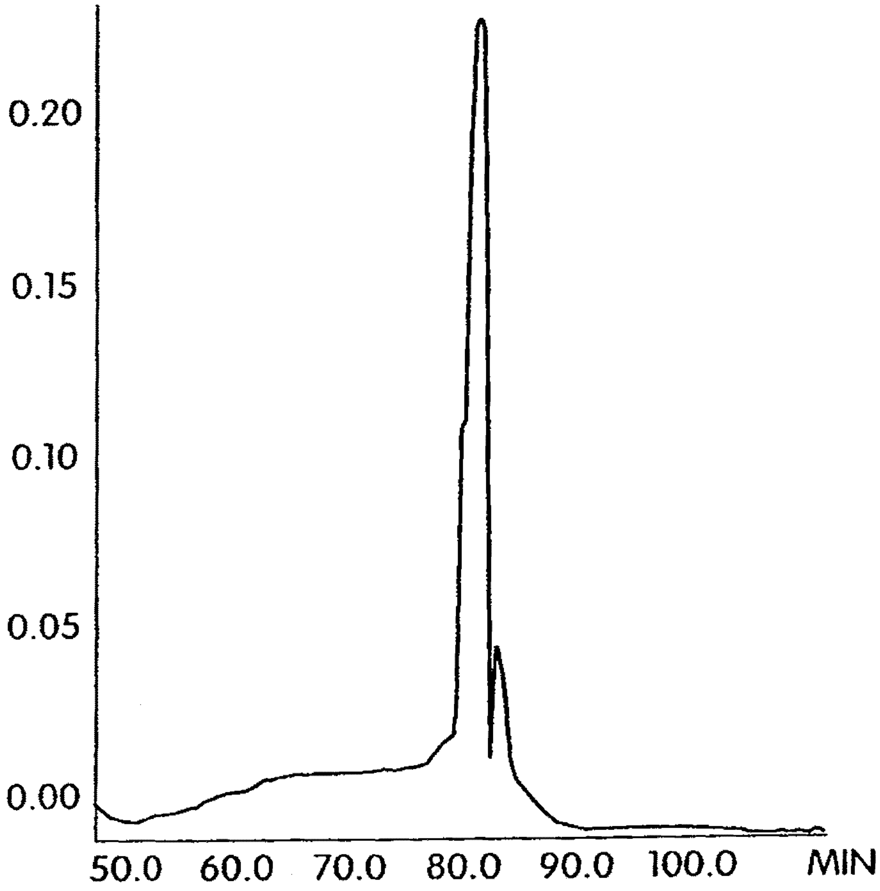

Definitions: As used herein, each of the following terms has the meaning associated with it in this section.

The term "serpin," as used herein, is intended to include native serpin polypeptide as well as any biologically active fragment(s) or analog(s) thereof. The terms "fragment" and "analog" are used interchangeably herein to describe serpins useful in the methods of the present invention.

The term "substantially pure," as used herein, describes a compound, e.g., a protein or polypeptide that has been separated from components, which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state. Included within the meaning of the term "substantially pure" as used herein is a compound, such as a protein or polypeptide, which is homogeneously pure, for example, where at least 95% of the total protein (by volume, by wet or dry weight, or by mole percent or mole fraction) in a sample is the protein or polypeptide of interest.

The term "specific binding" or "specifically binds," as used herein, means a protein, such as an antibody, which recognizes and binds a serpin, e.g., ATIII, or a ligand thereof, but does not substantially recognize or bind other molecules in a sample.

The term "pharmaceutically acceptable carrier," as used herein, means a chemical composition with which the active ingredient may be combined and which, following the combination, can be used to administer the active ingredient to a subject.

The term "physiologically acceptable" ester or salt, as used herein, means an ester or salt form of the active ingredient which is compatible with any other ingredients of the pharmaceutical composition, which is not deleterious to the subject to which the composition is to be administered.

The term "oily" liquid, as used herein, is one which comprises a carbon-containing liquid molecule and which exhibits a less polar character than water.

The term "additional ingredients," as used herein, include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants;

antibiotics; antifungal agents; stabilizing agents; and pharmaceutically acceptable polymeric or hydrophobic materials. Other "additional ingredients" which may be included in the pharmaceutical compositions of the invention are known in the art and described, for example, in Genaro, ed., 1985, REMINGTON'S PHARMACEUTICAL SCIENCES, Mack Publishing Co., Easton, Pa., which is incorporated herein by reference.

One "unit" of ATIII enzymatic activity, as used herein, is the activity present in 0.1 ml of normal human pooled plasma tested in the presence of 0.1 unit of heparin (Damus and Rosenberg, METH. ENZYMOL., 45. 653 (1976); PROTEOLYTIC ENZYMES: A PRACTICAL APPROACH, eds. Beynon and Bond, p. 247 (1989)). One "unit" of serpin enzymatic activity, as used herein, is understood to represent the conventional measure of serpin activity as defined in the art.

The term "transformation," as used herein, means introducing DNA into a suitable host cell so that the DNA is replicable, either as an extrachromosomal element, or by chromosomal integration.

The term "transfection," as used herein, refers to the taking up of an expression vector by a suitable host cell, whether or not any coding sequences are in fact expressed.

The term "infection," as used herein, refers to the introduction of nucleic acids into a suitable host cell by use of a virus or viral vector.

The term "antibody," as used herein, refers to an immunoglobulin molecule that is able to specifically bind to a specific epitope on an antigen.

I. HIV Inhibitors of the Present Invention

The present invention identifies antiretroviral activity of serpins (FIG. 1). The invention also includes methods for the treatment and prevention of HIV infection comprising contacting a composition of the invention with a human patient or treating HIV infection by introducing into a cell susceptible to HIV infection a DNA molecule encoding a serpin. Additionally, the invention includes antibodies and kits useful in the detection, treatment, and prevention of HIV infection.

Serpins constitute a superfamily of structurally related proteins found in eukaryotes, including humans (Wright, BIOASSAYS, 18: 453-64 (1996); Skinner et al., J. MOL. BIOL., 283: 9-14 (1998); Huntington et al., J. MOL. BIOL., 293: 449-55 (1999); Interpro #IPROO0215). Serpins are unusually large serine protease inhibitors, e.g., ATIII, protein C-inhibitor, activated protein C, plasminogen activator inhibitor, and alpha-1-antitrypsin. On a molar basis, inhibitory serpins comprise some 10 percent of human serum proteins.

While the Experimental Examples presented herein are directed to antithrombin (hereinafter, ATIII), it is contemplated that the present invention includes other serpins, as summarized in FIG. 1, or peptide fragment(s) derived therefrom or analog(s) thereof. In a preferred embodiment, the serpin binds heparin, and inhibits both serine protease and HIV. The term "serpin" encompasses naturally occurring serpins, as well as synthetic or recombinant serpins. Further, the term "serpin" encompasses allelic variants, species variants, and conservative amino acid substitution variants. The term also encompasses full-length serpins, as well as serpin fragments. It will thus be understood that fragments of serpins variants, in amounts giving equivalent biological activity to full-length serpins, can be used in the methods of the invention, if desired. Fragments of serpin incorporate at least the amino acid residues of serpins necessary for a biological activity similar to that of intact serpin. Examples of such fragments include the serpins presented in FIG. 1.

The term "serpin" also encompasses variants and functional analogs of serpins having a homologous amino acid sequence with a serpin. The present invention thus includes pharmaceutical formulations comprising such serpin variants and functional analogs, carrying modifications like substitutions, deletions, insertions, inversions or cyclisations, but nevertheless having substantially the biological activities of serpins.

According to the present invention, "homologous amino acid sequence" means an amino acid sequence that differs by one or more conservative amino acid substitutions, or by one or more non-conservative amino acid substitutions, deletions, or additions located at positions at which they do not destroy the biological activities of the polypeptide. Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine. Preferably, such a sequence is at least 75%, preferably 80%, more preferably 85%, more preferably 90%, and most preferably 95% homologous to the amino acid sequence of the reference Serpin.

Serpin structure is typified by a multi-domain fold containing a bundle of helices and a sandwich, and a welt-defined C-terminal reactive region that acts as a 'bait' for an appropriate serine protease. Many serpins are high molecular weight (400 to 500 amino acids), extracellular, irreversible inhibitors of serine proteases whose mechanism of inhibition involves dramatic conformational changes (Skinner et al., J. MOL. BIOL., 283: 9-14 (1998); Huntington et al., J. MOL. BIOL., 293: 449-55 (1999)). Significant tertiary structural changes may involve the insertion of the reactive center peptide loop insert into a gap in a major R-sheet forming a new strand (Stein and Carrell, NATURE STRUCT. BIOL., 2: 96-113 (1995); Sharp et al., STRUCTURE, 7: 111-8 (1999)). On the basis of strong sequence similarities, a number of proteins, e.g., angiotensinogen, thyroxine binding globulin, and corticosteroid binding globulin, with no known inhibitory activity, are said to belong to this family (Stein and Carrell, NATURE STRUCT. BIOL., 2: 96-113 (1995)).

Among the serpins, ATIII is a glycoprotein present in blood plasma with a well defined role in blood clotting. Specifically, ATIII is a potent inhibitor of the reactions of the coagulation cascade with an apparent molecular weight between 54 kDa and 65 kDa (Rosenberg and Damus, J. BIOL. CHEM., 248: 6490-505 (1973); Nordenman et al., EUR. J. BIOCHEM., 78: 195-204 (1977); Kurachi et al., BIOCHEMISTRY, 15: 373-7 (1976)) of which, some ten percent is contributed by four glucosamine-base carbohydrate chains (Kurachi et al., BIOCHEMISTRY, 15: 373-7 (1976); Petersen et al., IN THE PHYSIOLOGICAL INHIBITORS OF COAGULATION AND FIBRINOLYSIS, (Collen, Winman and Verstraete, eds) Elsevier, Amsterdam. p. 48 (1979)). Although the name, ATIII, implies that it works only on thrombin, it actually serves to inhibit virtually all of the coagulation enzymes to at least some extent. The primary enzymes it inhibits are factor Xa, factor IXa and thrombin (factor IIa). It also has inhibitory actions on factor XIIa, factor XIa and the complex of factor VIIa and tissue factor but not factor VIIa and activated protein C. ATIII also inhibits trypsin, plasmin and kallikrein (Charlotte and Church, SEMINARS IN HEMATOLOGY, 28:3-9

(1995). Its ability to limit coagulation through multiple interactions makes it one of the primary natural anticoagulant proteins.

ATIII acts as a relatively inefficient inhibitor on its own. However, ATIII can be activated by a simple template mechanism, or by an allosteric conformational change brought about by heparin binding (Skinner et al., J. MOL. B10L., 283: 9-14 (1998); Huntington et al., J. MOL. BIOL., 293: 449-55 (1999); Belar et al., J. BIOL. CHEM., 275: 8733-41 (2000)). When ATIII binds heparin, the speed with which the reaction that causes inhibition occurs is greatly accelerated; this makes the ATIII-heparin complex a vital component of coagulation. This interaction is also the basis for the use of heparin and low-molecular-weight heparins as medications to produce anticoagulation.

There is a growing body of evidence that ATIII has additional biological activity apart from its ability to inhibit thrombin. For example, ATIII has been demonstrated as an anti-inflammatory fraction in sepsis (Souter et at, CUT. CARE MED., 29: 134-9 (2001)), as an anti-angiogenesis factor in tumor growth (O'Reilly et at, SCIENCE, 285: 1926-8 (1999)), and is chemotactic to neutrophils through the sydecan-4 receptor (Dunzendorfer et at, BLOOD, 97: 1079-85 (2001); Kaneider et at, BIoCHEM. BwHYs. REs. CoM-MUN., 287: 42.6 (2001). The mechanism of action is so far not entirely clear.

A. Purification and Identification of mATIII

Activated $CD8^+$ T-cells produce at least two factors capable of inhibiting the X4 strain $HIV_{IIIB}$ (Geiben-Lynn et at, J. VIROL., 75: 8306-16 (2001)). These factors are distinct in their size and ability to bind heparin. One of these factor binds heparin at physiological salt concentration, elutes from a purification column at 350 mM NaCl, and is retained by a 50 kDa cut off Centricon filter. The other factor does not bind heparin at physiological salt concentration and passes through a 50 kDa cut off Centricon filter. The HIV inhibitory activity of these factors is higher with bulk $CD8^+$ T-cells of seropositive individuals and HIV specific Cytotoxic T-Lymphocytes (CTL) compared to bulk $CD8^+$ T-cells of HIV seronegative individuals (Geiben-Lynn et al., J. VIROL., 75: 8306-16 (2001)).

Figure 2B:
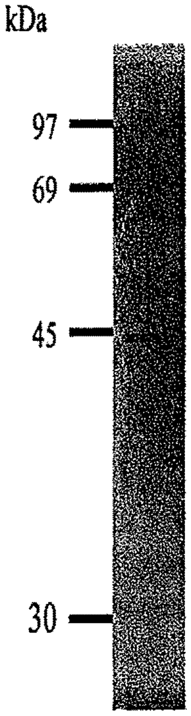

An X4 HIV inhibition assay (Geiben-Lynn et al., J. VIROL., 75: 8306-16 (2001); Shapiro et al., FASEB J., 15: 115-22 (2001)) was used to purify the inhibitory activity found in the heparin bound fraction of activated CD8+ T-cell supernatant (Geiben-Lynn et al., J. VIROL., 75: 8306-16 (2001)). The HIV inhibitory activity was purified to apparent homogeneity as measured by SDS-PAGE silver staining and C4-HPLC (Van Patten et al., J. BIOL. CHEM., 274: 10268-76 (1999)) using heparin Sepharose and Superdex-200 size-exclusion-chromatography (FIG. 2A). The HIV inhibitory factor was identified as a 43 kDa ATIII-like protein (mATIII; FIG. 2B), by reverse-phase HPLC nano-electrospray tandem mass spectrometry (μLC/MS/MS) on a Finnigan LCQ quadrupole ion trap mass spectrometer (FIG. 2C).

B. Characterization of the Antiretroviral Properties of ATIII Forms

Figure 3A:
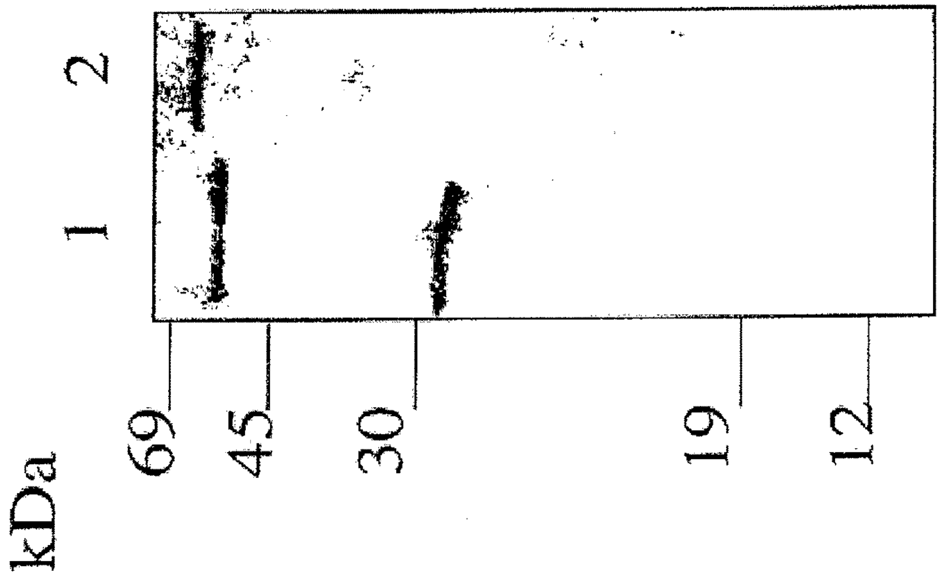
FIG. 3 demonstrates the antiviral effect of purified bovine ATIII on HIV. Panel 3A is a silver stained SDS-PAGE gel of R-ATIII (porcine elastase treated; lane 1) and S-ATIII (undigested; lane 2) used for the HIV inhibition tests Panel 3B is a graph comparing the HIV inhibitory activity of varying concentrations of R-ATIII and S-ATIII on X4 HIV and R5HIV infectivity, respectively. Virus inhibition was calculated using the buffer controls or the enzyme controls.

Analytical characterization of a CAF (Cf. FIG. 2) showed that activated CD8+ T-cells modify ATIII to mATIII, a form with enhanced ability to inhibit HIV infectivity. Therefore, the in vitro antiretroviral activity of ATIIII forms were measured and compared (FIGS. 3 and 4). Under physiological conditions, ATIII exists in different forms. In its most abundant configuration, ATIII circulates in a quiescent form, L-form, in which its reactive COOH-terminal loop is not fully exposed and cannot bind target proteins. When bound to heparin, a stressed confirmation, the S form of the molecule is induced: the reactive loop is exposed, and thrombin-binding affinity is increased by up to a factor of 100. The thrombin-ATIII complex then slowly dissociates, and the reactive loop of ATIII is cleaved by the released thrombin. The cleaved ATIII consists of disulfide-bonded A and B chains and does not bind target proteases. Additionally, this cleavage induces a conformational change to a relaxed confirmation, the R form, in which the reactive loop is irreversibly inserted into an A-beta sheet (Schreuder et al., NAT. STRUCT. BIOL., 1: 48-54 (1994)).

An R-ATIII form was described as an anti-angiogenetic factor capable of inhibiting tumor growth. This form of ATIII is cleaved between $Ser^{386}$ and $Thr^{387}$ and can be generated by digesting with porcine elastase (O'Reilly et al., SCIENCE, 285: 1926-8 (1999)). Other enzymes, which can cleave ATIII and produce R-ATIII forms are thrombin ($Arg^{394}$-$Ser^{395}$), pancreatic elastase ($Val^{388}$-$Iso^{389}$) and human neutrophil elastase ($Iso^{391}$-$Ala^{392}$) (Evans et al. BIOCHEMISTRY, 31: 12629-42 (1992); Mourey et at., J. MoL. BIOL., 232: 223-41 (1993)). A pre-latent ATIII, where the ATIII activity is still conserved and the heparin binding affinity is retained, can be produced through incubating S-ATIII at 60° C. for 24 h under physiological salt conditions (Larsson et al., J. BIOL. CHEM., 276: 11996-2002 (2001)).

To determine which form(s) of ATIII is capable of inhibiting retrovirus infectivity, the R-ATIII, pre-latent ATIII and L-ATIII were produced from a commercially available S-ATIII (serum purified bovine S-ATIII; Sigma Chemical Co., St. Louis, Mo., USA; 0.2-0.4 U/μg)). R-ATIII was obtained by incubating this S-ATIII (200 μg/ml) for at 37° C. in 20 mM Tris-HCl (pH 8.0) containing 150 mM NaCl and 2.5 U/ml porcine pancreatic elastase (CaibiochemNovabiochem Corporation, San Diego, Calif., USA; order No. 324682. Essentially complete conversion of S-ATIII to R-ATIII was obtained under these digestion conditions (FIG. 3A; O'Reilly et al., SCIENCE, 285:1926-8 (1999)). In select studies, S-ATIII was digested in PBS using an immobilized V-8 Protease Kit (PIERCE) for 1 h at 4° C., according manufacturer's procedure.

X4 HTLV-IIIB (hereinafter X4 HIV; Chang et al., NATURE, 363: 466-9 (1993)), a prototypical T-tropic strain of HIV (American Type Tissue Collection, Monassass, Va., USA; ATCC No. CRL-8543), was used to assess the effect of ATIII on T-tropic HIV infection. The quantity of virus in a specified suspension volume (e.g., 0.1 ml) that will infect 50% of a number (n) of cell culture microplate wells, or tubes, is termed the Tissue Culture Infectious Dose 50 [$TCID_{50}$]. $TCID_{50}$ is used as an alternative to determining virus titre by plaqueing (which gives values as PFUs or plaque-forming units). Karber, 1931.

Human T lymphoblastoid cells (H9 cells) expressing the human leukocyte antigen proteins (HLA) B6, Bw62, and Cw3 were acutely infected with X4 HIV at a MOI of $1\times10^{-2}$ $TCID_{50}$ per milliliter. The infected H9 cells were resuspended to $5\times10^5$ cells/ml in R20 cell culture medium. Two milliliters of this suspension was pipetted into each well of a 24-well microtiter plate.

PM1 macrophage-like-cells were acutely infected with R5 $HIV_{JR-CSF}$ (hereinafter R5 HIV; Koyanagi, et al., SCIENCE, 236: 819-22, (1987)) to examine the ability of ATIII to affect monocytropic HIV infection. The R5HIV isolate, JR-CSF was originally obtained from the cerebrospinal fluid of an HIV-infected individual at autopsy. This strain shows properties characteristic of a primary HIV isolates, e.g., it replicates efficiently in primary blood cells but not in cell lines. That is, JR-CSF exhibits properties more characteristics of clinical HIV isolates obtained directly from the HIV patient.

It is now a standard reference strain representing macrophage tropic strains of HIV. PM1 cells were acutely infected with $HIV_{IIIB}$ at a MOI of $1\times10^{-2}$ $TCID_{50}$ per milliliter.

Simian immunodeficiency virus (SIV) belongs to the family Retroviridae (subfamily Lentivirinae) and is closely related to human immunodeficiency virus types 1 and 2 (HIV-1 and HIV-2), the etiologic agents of AIDS. Originally reported in 1985, the first isolate from a rhesus macaque was called simian T-lymphotropic virus III (STLV-III). The SIVmac239 viral strain (hereinafter $SIV_{239}$; P. Johnson, Harvard Medical School, Boston, Mass., USA) used in these studies is a dual-tropic infectious virus that induces AIDS in rhesus macaque monkeys.

$SHIV_{KU-1}$ (Narayan and Joag, AIDS Research and Reference Program, Division of AIDS, NIADS, Bethesda, Md., USA) is a second dual-tropic strain of SIV used in these studies. $SHIV_{KU-1}$ is a biologically-pure suspension of SHIV that is highly pathogenic in pigtailed macaques. The virus was derived by sequential passage of the molecular construct of SIV(mac)239XHIV-1-HxB2 through bone marrow of pigtailed macaque monkeys (Joag et al, J. VIROLOGY, 70:3189-3197 (1996)).

The cell tropism of SIV in culture depends partially on the strain of virus propagated and conditions of cell culture. In the present studies, macaque T-cell line SEM-174 cells were acutely infected with either $SIV_{239}$ or $SHIV_{KU-1}$ at a MOI of $1\times10^{-2}$ $TCID_{50}$ per milliliter.

Figure 3B:
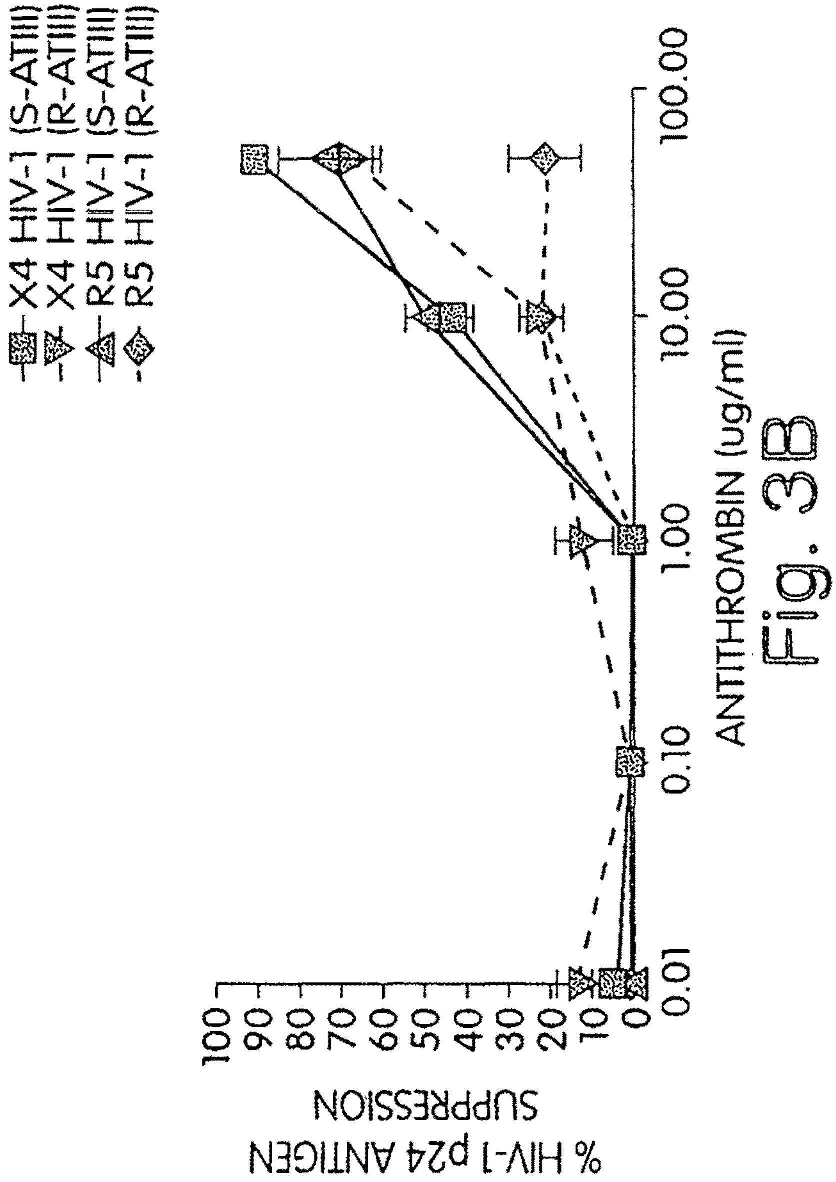

As shown in FIG. 3B, R-ATIII inhibited X4 virus with half-maximal inhibition ($ID_{50}$) at approximately 25 μg/ml. The S-ATIII was more potent than R-ATIII and displayed, with an $ID_{50}$ at 10 μg/ml (~3 U/ml), activity comparable to the $CD8^+$T-cell modified form of ATIII (FIG. 3B). This is similar to the $ID_{50}$ (5.5 μg/ml), which was measured for the mATIII and with 130 nM similar to that found for Stromal-Derived-Factor (SDF-1), the only natural occurring ligand found binding the CXCR4 coreceptor. (Geiben-Lynn et al., J. VIROL., 75: 8306-16 (2001)).

Figure 4A:
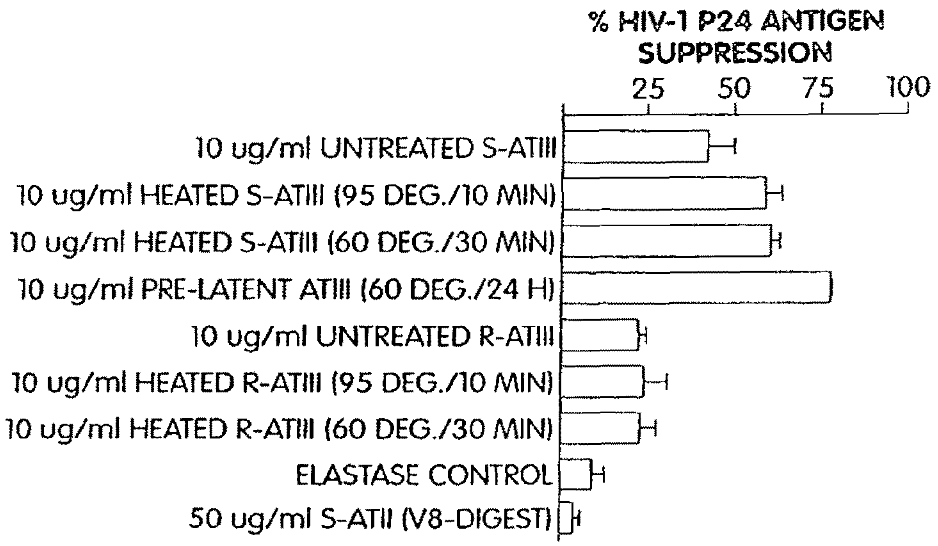
FIG. 4A is a graph comparing the effect of heat treatment (95° C., 10 min and 60° C., 30 min treatment) on R- and S-ATIII-mediated X4 HIV inhibition using porcine elastase alone as an experimental control. The inhibitory activity of a pre-latent ATIII (60° C., 24 h), and S-ATIII pretreated with V8 protease were also tested.
Figure 4B:
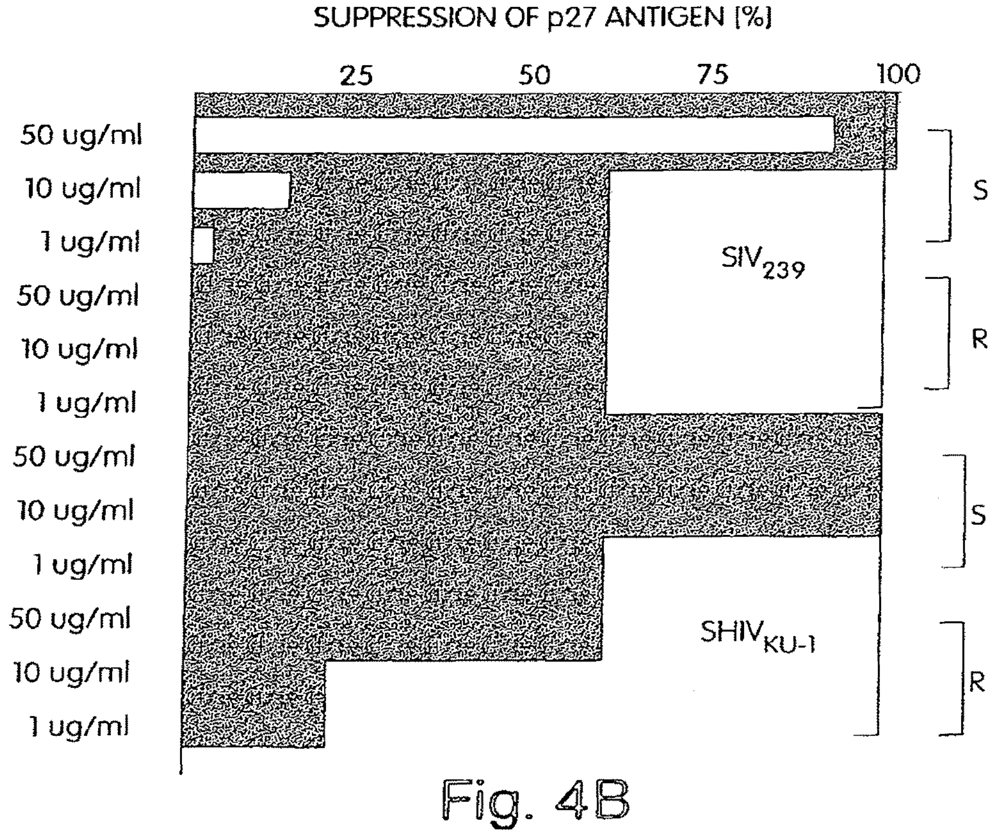
FIG. 4B is a graph comparing HIV inhibitory activity of R-ATIII and S-ATIII on SIV and SHIV ($SIV_{KU-1}$) infectivity. Virus inhibition was calculated using the buffer controls or the enzyme controls.
Figure 5:
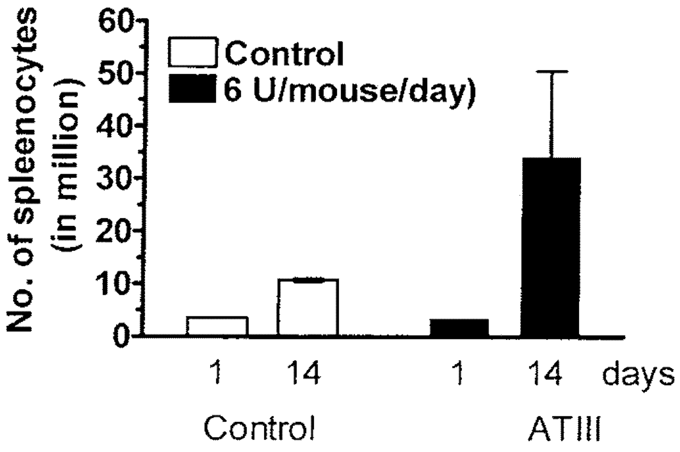
FIG. 5 is a graph showing in vivo protection of human peripheral blood mononuclear cells (PBMC) during treatment with Antithrombin III (ATIII) in NOD Cg-prkc-b2m−/− mice. $10^7$ PBMC were infected with multidrug resistant HIV (100 ng p24) and incubated at 37° C. for 1 hour. $3.5\times10^6$ in vitro infected PBMC were administered intra peritoneal into a NOD Cg-prkc-b2m−/− mice (n=5) and treated daily with 6 Units of ATIII. Spleens were harvested at 14 days and number of cells were counted under a light microscope. The data are expressed as mean (±standard errors of the means).
Figure 6:
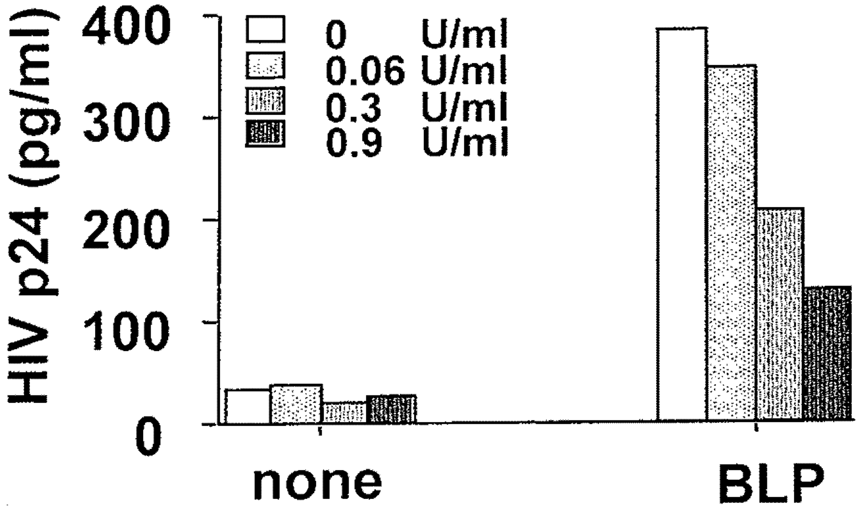
FIG. 6 is a graph showing suppression of HIV-1 expression in TLR2 stimulated Tg cells. $5\times10^6$/ml spleenocytes of Tg mouse line 166 (Freitag et. al., 2001, J. Infect. Dis. 183, 1260-1268 (2001)), which contains multiple copies of the complete proviral genome of HIV-1 strain NL4-5 were incubated with 10 ng/ml bacterial lipoprotein (BLP) Pam3CSK4 (InvivoGen, San Diego, Calif.), a TLR2 agonist, and different amounts of ATIII (0, 0.06, 0.3, 0.9 U/ml) for 48 hours (n=2). P24 HIV antigen was then assayed by enzyme-linked immunosorbent assay (ELISA) in supernatants at 48 h using a commercial kit (p24 Coulter, Miami, Fla.).
Figure 7:
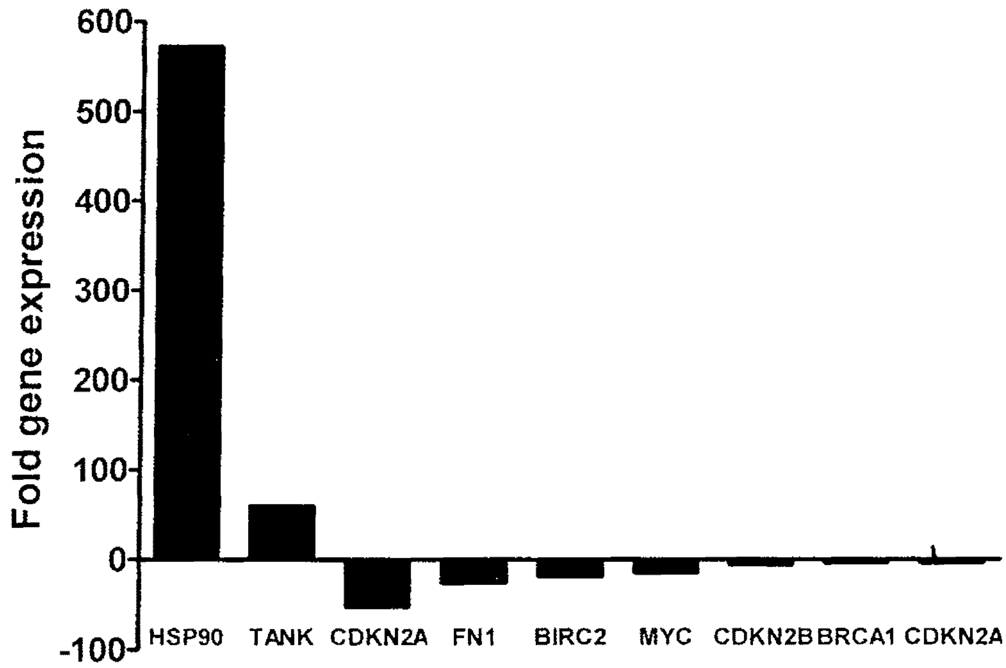
FIG. 7 is a graph showing changes in gene expression patterns of human PBMC after infection with HIV-1 but without treatment of ATIII. $10^5$ human PBMC were acutely infected by HIV-1 for 1 h at 37° C., cells were washed and incubated for 40 h. Superarray's Pathfinder Array™ (SABiosciences, Frederick, Md.) was used to measure gene expression (n=3). Only significant changes ($p<0.05$) are shown.
Figure 8:
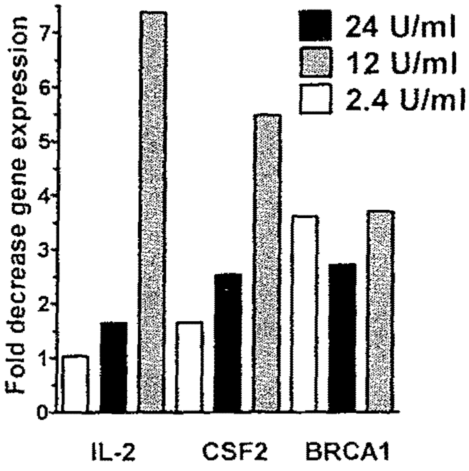
FIG. 8 is a graph showing changes in gene expression patterns of human PBMC after treatment with ATIII but without infection with HIV-1. $10^5$ human PBMC were treated with 2.4, 12 and 24 U ATIII/ml for 40 h. Superarray's Pathfinder Array™(SABiosciences) was used to measure gene expression (n=3). Only significant changes ($p<0.05$) are shown.
Figure 9:
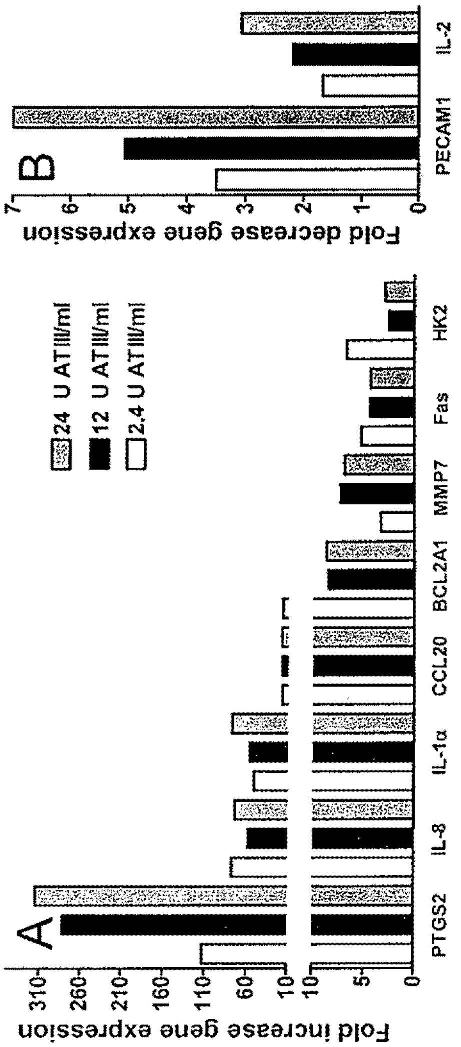
FIG. 9 is a graph showing changes in gene expression patterns of human PBMC after infection with HIV-1 and treatment with ATIII. $10^5$ human PBMC were acutely infected by HIV-1 for 1 h at 37° C., cells were washed and treated with 2.4, 12 and 24 U ATIII/ml for 40 h. Superarray's Pathfinder Array™ (SABiosciences) was used to measure increase (A) or decrease in gene expression (n=3). Only significant changes ($p<0.05$) are shown.
Figure 10:
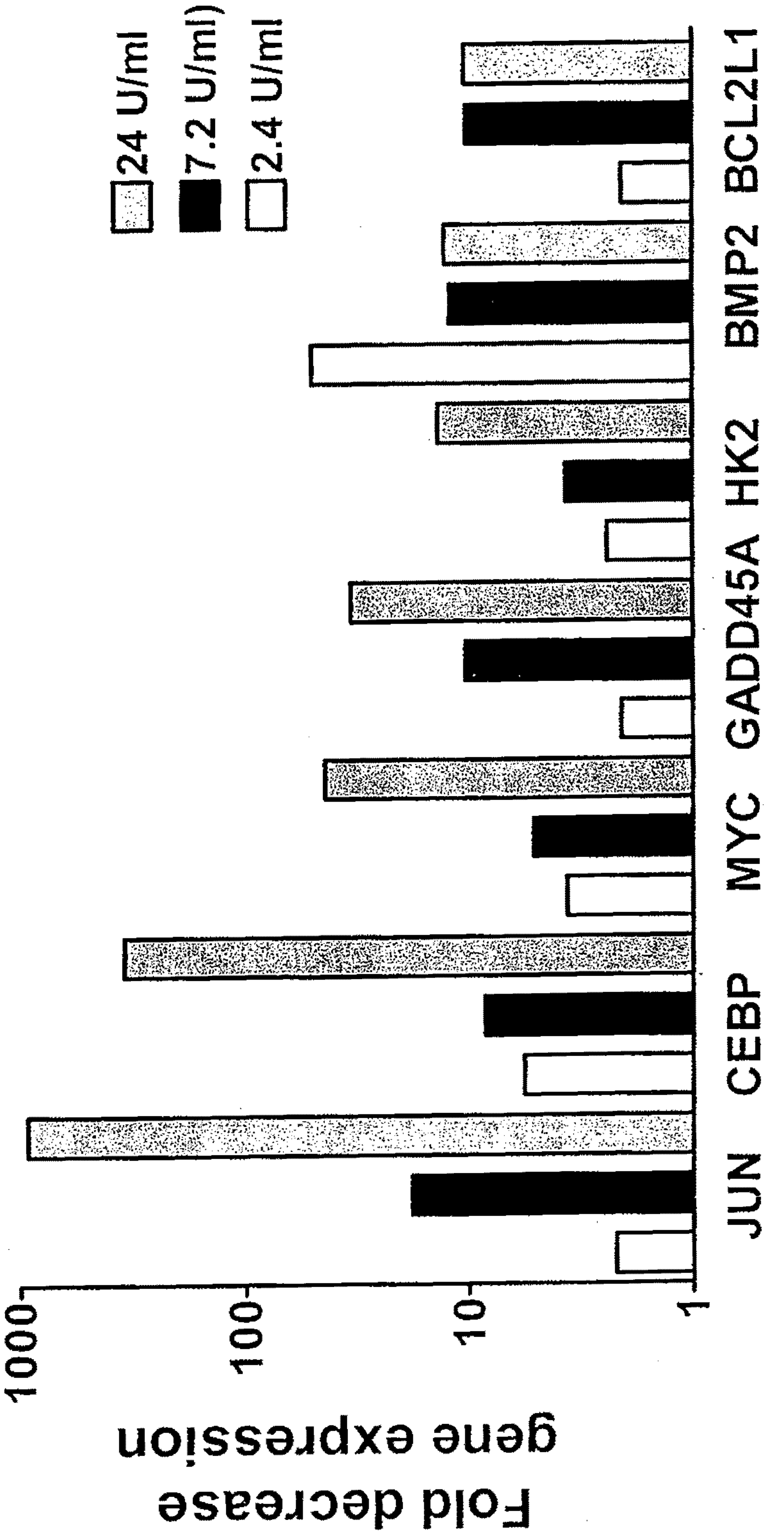
FIG. 10 is a graph showing changes in gene expression patterns HCV replicon after with ATIII. $10^4$ HCV replicon cells were treated with 2.4, 7.2 and 24 U ATIII/ml for 40 h. Superarray's Pathfinder Array™ (SABiosciences) was used to measure gene expression (n=3). Only significant changes ($p<0.05$) are shown.
Figure 11:
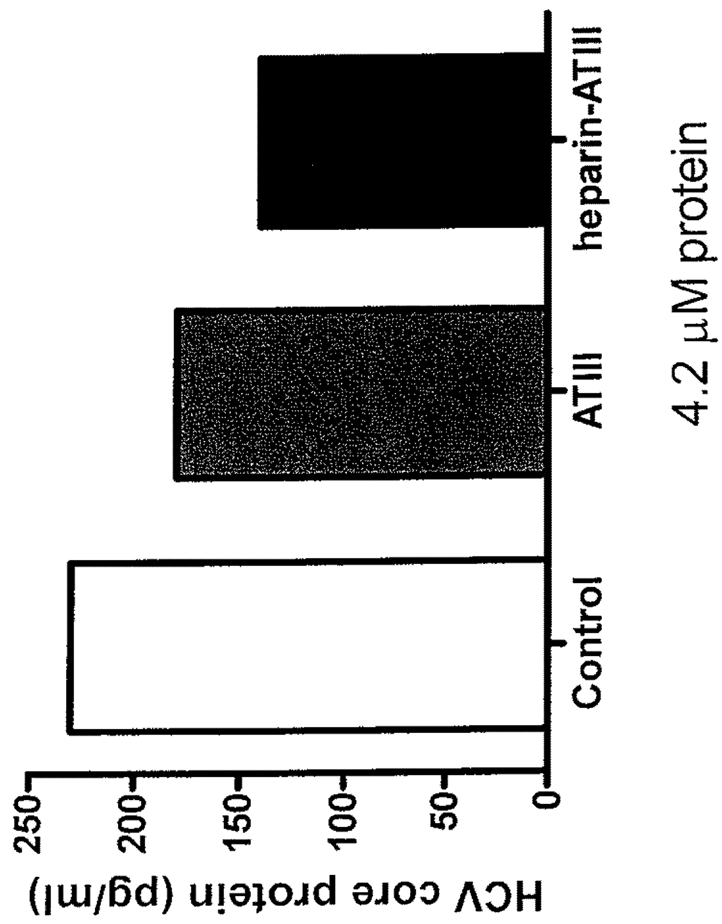
FIG. 11 is a graph showing the antiviral effect of ATIII and heparin-ATIII complex on HCV.

As shown in FIG. 4, S-ATIII and R-ATIII-mediated antiviral activity was resistant to inactivation by heat-treatment, as well as pre-latent ATIII inhibited X4 HIV infectivity (FIG. 4A). ATIII-mediated antiretroviral activity was not due to cytotoxicity because ATIII treatment did not affect cell viability or cell growth as judged by Trypan blue dye exclusion (data not shown). At a concentration of 50 μg/ml (15 U/ml), the S-ATIII inhibited SIV and HSIV infectivity by 92 and 91%, respectively (FIG. 4B). R-ATIII inhibited the simian retroviral strains to a lesser extent with 36 and 57% suppression of SIV core protein (p27), respectively (FIG. 4B).

This purified protein was of similar molecular size, but was not the same as a previously described $CD8^+$T-cell antiviral factor, CAF (Levy et al., IMMUNOL. TODAY, 17: 217-24 (1996)). That is, the purified ATIII-like protein of the present invention is similar in size to CAF and its ability to inhibit X4 viruses but different in regard to heat stability (Geiben-Lynn et at, J. VIROL., 75: 8306-16 (2001)). CAF has not been defined at a molecular level, however, and it has only been tested as an unfractionated supernatant. The anti-HIV activity of CAF may reflect multiple factors involved with different points of inhibition in the life cycle of HIV.

Purified $CD8^+$ T-cell ATIII is a molecularly distinct form of ATIII. Native, unmodified ATIII has a molecular weight of 54-65 kDa, whereas the purified ATIII form $CD8^+$ T-cells was 43 kDa as judged by SDS-PAGE analysis. Purified $CD8^+$ T-cell ATIII is smaller than the S-ATIII and elutes from a heparin Sepharose column at lower salt concentration (350 mM NaCl versus 1 M NaCl). Purified $CD8^+$ T-cell ATIII is also smaller that R-ATIII and does not dissociate under reducing conditions used in the SDS-PAGE. Finally, purified $CD8^+$ T-cell ATIII and pre-latent ATIII displayed similar anti-HIV potency in vitro but they differ in molecular weight.

Under the conditions of enzyme pretreatment, V8 protease preferentially digests the heparin-binding domain of ATIII. Accordingly, the lack of antiretroviral activity in ATIII preparation pretreated with V8 protease suggests that the heparin-binding domain of ATIII is important for antiviral activity (FIG. 4A). ATIII has been shown to bind to the syndecan family of proteoglycans, which may mediate these biological activities. In this regard, HIV, SIV, and SHIV have a requirement for syndecans for attachment which facilitate HIV/SIV entry into cells (Valenzuela-Fernandez et at, J. BIOL. CHEM., 276: 26550-8 (2001); Saphire et at, J. VIROL., 75: 9187-200 (2001)). ATIII appears to interact with the HIV-syndecan binding domain and that ATIII inhibits HIV entry into cells, which might be synergistic with other pathways. As such, ATIII and other serine protease inhibitors offer the potential for improved efficacy and diminished toxicity in the treatment of HIV and other viral diseases.

II. Use of the Present Invention for the Treatment, Prevention and Detection of Retroviral Infection The invention includes the use of a composition comprising substantially purified ATIII. ATIII is capable of inhibiting the infectivity of HIV as described herein, and thus is useful in methods for the prevention of HIV infection in a patient or for inhibiting the infectivity of HIV containing bodily fluids. The ATIII to be used in the present invention is not particularly limited as long as it has been purified to the extent that it can be used as a pharmaceutical agent. For example, it can be purified from whole blood, blood plasma, serum or serum obtained by compression of coagulated blood. The starting material for preparing ATIII may be, for example, fraction IV-1 or IV, or supernatant I or II+III obtained by Cohn's fractionation of blood plasma. ATIII can also be prepared by, for example, *E. coli*, cell culture (e.g., EP-339919 to Isahiko et al.), genetic engineering (e.g., EP-90505 to Botsuku and Roon), transgenic animal (Larrik and Thomas, CURB. OPIN. BIOTECHNOL. 12: 41111-41118 (2001); Edmunds et al., BLOOD 12: 4561-4571 (1998)), and the like. Alternatively, a commercially available ATIII preparation can be used.

Compositions comprising substantially purified ATIII may include ATIII alone, or in combination with other proteins. ATIII may be substantially purified by any of the methods well known to those skilled in the art. Substantially pure protein may be purified by following known procedures for protein purification, wherein an immunological, chromatographic, enzymatic, or other assay is used to monitor purification at each stage in the procedure. Protein purification methods are well known in the art, and are described, for example in Deutscher et al., GUIDE TO PROTEIN PURIFICATION, Harcourt Brace Iovanovich, San Diego (1990). ATIII can be purified by a method described in, for example, U.S. Pat. No. 3,842,061 to Anderson et al. and U.S. Pat. No. 4,340,589 to Uemura et al.

In one embodiment, the ATIII of the invention is a component of a pharmaceutical composition, which may also comprise buffers, salts, other proteins, and other ingredients acceptable as a pharmaceutical composition. The invention also includes a modified form of ATIII, which is capable of contacting HIV and inhibiting the infectivity of HIV as described herein. The modified ATIII may be used as a component of a composition for use in a method for prevention of HIV infection of a patient or in the inhibition of HIV infectivity of biological fluids.

The ATIII of the invention may be a molecule that comprises the protein alone, or may include other components, such as protein or other carbohydrate, or another molecule that may be covalently linked to the ATIII, or may be non-covalently associated with the ATIII.

The ATIII of the invention may be generated by enzymatic digestion or chemical treatment of the full protein ATIII. Chemical treatment methods may include, for example, digestion using mild acid hydrolysis, treatment with 0.9 M guanidine (Carrell et al., NATURE, 353: 576-8 (1991)) or incubating S-ATIII in 0.25 mM trisodium citrate at 60° C. for 18 hours (Wardell et al., BIOCHEMISTRY, 36: 13133-42 (1997)). Enzymatic digestion methods may include, for example, digestion using an elastase or other protease. Enzymatic digestion methods may also include, for example, digestion using a specific exoglycosidase (e.g., neuraminidase, mannosidase, fucosidase) or a specific endoglycosidase (e.g., N-glycanase, O-glycanase).

In another embodiment, the ATIII of the invention may be prepared using a biochemical synthesis method. Biochemical methods for synthesizing proteins are well known to those skilled in the art.

The ability to contact HIV virion may be assessed using assays described herein in the Examples section. For example, the virus may be incubated with the molecule comprising an ATIII of the invention, placed over a sucrose cushion, and centrifuged. The virus pellet obtained is resuspended, concentrated with trichloroacetic acid (TCA) to concentrate the proteins, and aliquots of the pellet and supernatant are analyzed by Western blotting using antibodies to p24 (Nagashurmugam and Friedman, DNA CELL BIOL. 15: 353-61 (1996)) or by an ELISA method.

In yet another embodiment, the molecule comprising the ATIII of the invention is capable of inhibiting the infectivity of HIV in a patient by contacting an HIV virion. The molecule comprising the ATIII of the invention is included as a component in a pharmaceutical composition that may be administered to a patient to inhibit HIV infectivity or to prevent infection by HIV. The inhibition of infectivity of HIV by the molecule comprising the ATIII of the invention may be assessed as described herein. Such methods may include p24 assay, reverse transcriptase activity assay, or $TCID_{50}$.

The invention also includes an antibody that is capable of specifically binding to ATIII. The antibody of the invention may be a monoclonal or a polyclonal antibody, or may be a synthetic, humanized or phage displayed antibody. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1988, ANTIBODIES: A LABORATORY MANUAL, Cold Spring Harbor, N.Y.; Houston et al., PROC. NATL. ACAD. SCI. USA 85: 5879-83 (1988); Bird et al., SCIENCE, 242: 423-6 (1988)). By the term “synthetic antibody” as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The invention also includes a kit for detecting a protein that inhibits the infectivity of HIV. The proteins include ATIII. The kit of the invention, may, for example, be an ELISA kit, which includes an antibody, a detection reagent, and a reaction surface. In one embodiment, the antibody is an antibody of the invention that specifically binds with ATIII. The antibody may be any type of antibody described herein and may be made using any of the methods described herein. The reaction surface may be a microtiter plate, such as an ELISA plate. The detection reagent may be any detection reagent known to those skilled in the art. For example, the detection reagent may be an enzyme, or a radionucleotide. In one embodiment, the kit of the invention is an ELISA kit for detecting the presence of ATIII in a bodily fluid such as serum of a human patient.

The kit may include a microwell plate, an antibody that is capable of specifically binding either ATIII, and a secondary enzyme capable of binding the antibody of the invention and also horseradish peroxidase. The ELISA kit of the invention may be used, for example, to carry out an ELISA assay of a bodily fluid of a patient, such as a serum sample. The assay may be used to detect and quantify levels of ATIII present in the serum of the patient. The quantity of ATIII in the patient’s serum may be correlated with the ability of the patient’s serum to inhibit the infectivity of HIV.

In another embodiment, the kit of the invention is a Western Blotting or dot blotting kit for detecting the presence of ATIII in a bodily fluid such as serum of a human patient.

The kits of the present invention may be used, for example, to assess the susceptibility of a patient to HIV infection. Patients with high susceptibility to HIV infection due to low levels of ATIII may be treated with one of the pharmaceutical compositions of the invention to enhance resistance of these individuals to HIV infection. The correlation between the levels of ATIII with the ability of a patient to inhibit the infectivity of HIV is established using the procedures described in the Experimental Examples presented herein.

The invention also includes a method of inhibiting the infectivity of HIV in bodily fluids, or in infective oral secretions. The method is useful in preventing HIV infection, or inhibiting the infectivity of HIV. This method can be used, for example to inhibit the infectivity of biological fluids, for example in a hospital setting where medical personnel are exposed to infectious HIV secretions.

In one embodiment, the method comprises contacting an HIV virion with the human ATIII compositions described herein. In one embodiment, the ATIII composition may comprise substantially purified ATIII. The sample from a patient containing the HIV virion may be obtained from any sample of bodily fluid, such as blood, plasma, serum, semen, cervical secretions, saliva, urine, breast milk, or amniotic fluids. In one embodiment, a composition comprising substantially purified ATIII is contacted with an HIV virion from a sample of a patient for a period of time sufficient for the ATIII to inhibit the infectivity of HIV. The inhibition of the infectivity of HIV can be assessed as described herein in the Examples.

In another embodiment, the method of inhibiting the infectivity of HIV comprises contacting an HIV virion obtained from a bodily fluid sample of a patient with a composition having a surface which contains a substantially purified human ATIII associated with said surface. Examples of such surfaces include plastic or other polymer surfaces, which are inert to reaction with bodily fluids, and are considered biocompatible. In one embodiment of the method of the invention, the composition having substantially purified human ATIII associated with the surface is contacted with a body fluid of a patient or an infective oral secretion that contains an HIV virion. The composition is contacted or incubated with the sample of bodily fluid containing the HIV virion for a period of time sufficient to inhibit the infectivity of HIV. The inhibition of the infectivity of HIV can be assessed as described herein in the Examples section. For example, parameters that are used to assess HIV replication, such as, for example, the presence or absence of HIV specific components, such as nucleic acid or protein, or in the latter case, the activity of HIV specific components, such as reverse transcriptase, may be used to assess inhibition of HIV in a sample.

The invention encompasses the preparation and use of pharmaceutical compositions comprising a compound useful for the prevention of HIV infection or inhibition of HIV infectivity as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art. Further, the ATIII (or biologically active analog thereof) used in the present invention may contain pharmacologically acceptable additives (e.g., carrier, excipient and diluent), stabilizers or components necessary for formulating preparations, which are generally used for pharmaceutical products, as long as it does not adversely affect the object of the present invention.

Examples of the additives and stabilizers include saccharides such as monosaccharides (e.g., glucose and fructose), disaccharides (e.g., sucrose, lactose and maltose) and sugar alcohols (e.g., mannitol and sorbitol); organic acids such as citric acid, malic acid and tartaric acid and salts thereof (e.g., sodium salt, potassium salt and calcium salt); amino acids such as glycine, aspartic acid and glutamic acid and salts thereof (e.g., sodium salt); surfactants such as polyethylene glycol, polyoxyethylene-polyoxypropylene copolymer and polyoxyethylenesorbitan fatty acid ester; heparin; and albumin.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, the skilled artisan will understand that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. The preferred mode is intravenous administration.

The ATIII and the above-mentioned ingredients are admixed as appropriate to give powder, granule, tablet, capsule, syrup, injection, and the like. Other contemplated formulations include projected nanoparticles, liposomal preparations, resealed erythrocytes containing the active ingredient, and immunologically based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers. Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108 to Theeuwes; 4,160,452 to Theeuwes; and 4,265,874 to Bonsen et al., to form osmotically controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and acetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, a gel or cream or solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but mot limited to, antioxidants, antibiotics, antifungal agents, and preservatives.

Additional delivery methods for administration of compounds include a drug delivery device, such as that described in U.S. Pat. No. 5,928,195 to Malamud et al.

As used herein, “parenteral administration” of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer’s solution, isotonic sodium chloride solution, and fixed oils such as synthetic mono- or di-glycerides. Other parentally-administrable formulations that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or. semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations that are useful include those which comprise the active ingredient in microcrystalline form or in a liposomal preparation.

The mixture of ATIII and pharmacologically acceptable additives is preferably prepared as a lyophilized product, and dissolved when in use. Such preparation can be prepared into a solution containing about 1-100 units/ml of ATIII, by dissolving it in distilled water for injection or sterile purified water. More preferably, it is adjusted to have a physiologically isotonic salt concentration and a physiologically desirable pH value (pH 6-8).

ATIII has been shown to be well-tolerated when administered at a dose of ~100 U/kg/day (Warren et al., JAMA 286: 1869-78 (2001)) and has an overall elimination half-life with 18.6 h was demonstrated (Ilias et al., INTENSIVE CARE MEDICINE 26: 7104-7115 (2000)). While the dose is appropriately determined depending on symptom, body weight, sex, animal species and the like, it is generally 1-1,000 units/kg body weight/day, preferably 10-500 units/kg body weight/day of ATIII for a human adult, which is administered in one to several doses a day. In the case of intravenous administration, for example, the dose is preferably 10-100 units/kg body weight/day. The compound may be administered as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The present invention further provides host cells genetically engineered to contain the polynucleotides encoding ATIII or analogs of ATIII and expressing the ATIII polypeptide in an amount sufficient to inhibit infection of the cell by HIV. Still further, the present invention provides a method of treating HIV infection in a subject, introducing into the subject a producer cell that expresses ATIII in a sufficient amount to inhibit infection of an endogenous cell of the subject. For example, such host cells may contain nucleic acids encoding ATIII and introduced into the host cell using known transformation, transfection or infection methods. The present invention still further provides host cells genetically engineered to express the polynucleotides of ATIII, wherein such polynucleotides are in operative association with a regulatory sequence heterologous to the host cell, which drives expression of the polynucleotides in the cell. See, for example, U.S. Pat. No. 4,632,981 to Bock and Lawn; and EP-90505 to Botsuku and Roon.

Knowledge of ATIII nucleic acid sequences allows for modification of cells to permit, or increase, expression of endogenous polypeptide. Cells can be modified (e.g., by homologous recombination) to provide increased polypeptide expression by replacing, in whole or in part, the naturally occurring promoter with all or part of a heterologous promoter so that the cells express the polypeptide at higher levels. The heterologous promoter is inserted in such a manner that it is operatively linked to the encoding sequences. See, for example, PCT International Publication No. WO94/12650 by Hartlein et al., PCT International Publication No. WO 92/20808 by Smithies, and PCT International Publication No. WO 91/09955 by Chappel. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the coding sequence, amplification of the marker DNA by standard selection methods results in co-amplification of the desired protein coding sequences in the cells.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis et al., BASIC METHODS IN MOLECULAR BIOLOGY (1986)). The host cells containing a polynucleotide encoding ATIII, can be used in conventional manners to produce the gene product encoded by the isolated analog or fragment (in the case of an open reading frame) or can be used to produce a heterologous protein under the control of the EMF.

Any host/vector system can be used to express one or more ATIII protein forms. Potential hosts include, but are not limited to, eukaryotic hosts such as HeLa cells, Cv-1 cell, COS cells, 293 cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., in MOLECULAR CLONING: A LABORATORY MANUAL, SECOND EDITION, COLD SPRING HARBOR, NEW YORK (1989), the disclosure of which is hereby incorporated by reference.

Various mammalian cell culture systems can also be employed to express recombinant ATIII protein. Examples of mammalian expression systems include the COS-7 lines of monkey kidney fibroblasts, described by Gluzman, CELL, 23:175-82 (1981). Other cell lines capable of expressing a compatible vector are, for example, the C127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Mammalian expression vectors will comprise an origin of replication, a suitable promoter and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

The present invention also provides a method of treating HIV infection where a DNA encoding a serpin, e.g., ATIII, or analog thereof, is introduced into a cell susceptible to HIV infection and expressed in a sufficient amount to inhibit infection of the cell by the HIV. That is, the invention provides gene therapy to treat retrovirus-induced disease states involving serpin, e.g., ATIII. Delivery of a functional gene encoding serpin to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, NATURE, 392(6679Suppl.): 2530 (1998); see also, Friedmann, SCIENCE, 244: 1275-81 (1989); Verma, Sa. Am., 263: 68-84 (1990); Miller, NATURE, 357: 455-60 (1992). Introduction of a serpin gene encoding the can also be accomplished with extrachromosomal substrates (transient expression) or artificial chromosomes (stable expression). Cells may also be cultured ex vivo in the presence of serpin in order to proliferate or to produce a desired effect on or activity in such cells. Treated cells can then be introduced in vivo for therapeutic purposes. Alternatively, it is contemplated that antisense therapy or gene therapy could be applied to negatively regulate the expression of serpins of the invention.

Other methods inhibiting expression of a protein include the introduction of antisense molecules to the nucleic acids of the present invention, their complements, or their translated RNA sequences, by methods known in the art. Further, the serpins can be inhibited by using targeted deletion methods, or the insertion of a negative regulatory element such as a silencer, which is tissue specific.

The present invention still further provides cells genetically engineered in vivo to express polynucleotides encoding serpin, e.g., ATIII, wherein such polynucleotides are in operative association with a regulatory sequence heterologous to the host cell which drives expression of the polynucleotides in the cell. These methods can be used to increase or decrease the expression of the serpin polynucleotides.

In another embodiment of the present invention, cells and tissues may be engineered to express an endogenous gene comprising serpin, e.g., ATIII, under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequence include polyadenylation signals, mRNA stability elements, splice sites, leader sequences for enhancing or modifying transport or secretion properties of the protein, or other sequences which alter or improve the function or stability of protein or RNA molecules.

In all the above embodiments involving augmentation of cellular serpin, e.g., ATIII, expression, the targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; international Application No PCT/US92/09627 (WO93/09222) by Selden et al.; and International Application No. PCT/US90/06436 (WO91/06667) by Skoultchi et al., each of which is incorporated by reference herein in its entirety.

The present invention is described in more detail in the following by illustrative Examples, to which the present invention is not limited.

EXAMPLES

These Examples are provided for the purpose of illustration only and the invention should in no way be construed as being limited to these Examples, but rather should be construed to encompass any and all variations which become evident as a result of the teaching provided herein.

Example 1

HPLC Purification of an HIV Inhibitory Factor from $CD8^+$ T-Cells and its Identification as an Antithrombin III Using Nano-Electrospray Tandem Mass Spectrometry To purify the ATIII-like HIV inhibitory factor, HIV-specific CTL or bulk $CD8^+$ T-cells of long-term non-progressors were cultivated in vitro and stimulated with CD3 crosslinking (Geiben-Lynn et al., J. VIROL., 75: 8306-16 (2001)) in either 10% heat-inactivated fetal bovine serum or 10% heat-inactivated human serum. After 4 h at 37° C., media was collected, centrifuged, and applied to a heparin Sepharose column. The column was eluted with a continuous gradient to 1 M NaCl in phosphate-buffered saline (PBS, pH 7.4). Inhibitory fractions were pooled, and concentrated with a Centricon 50K centrifugal concentrator. The sample was applied to a Superdex 200 column. Fractions that inhibited were applied to a Vydac RP-4 HPLC column equilibrated with distilled water and 0.1% (v/v) trifluoroacetic acid (TFA) and tested for purity (FIG. 2A). Bound protein was eluted with a gradient of acetonitrile in TFA (Van Patten et al., J. BIOL. CHEM., 274: 10268-76 (1999)). Additionally, the purity of the final samples were assessed by SDS-polyacrylamide gel electrophoresis (PAGE) with silver staining, and the protein concentration was determined with a Bio-Rad protein assay. Fractions with >95% purity by C4-HPLC and silverstaining were used for the inhibition tests to determine the $ID_{50}$ (Schreuder et al., NAT. STRUCT. BIOL., 1: 48-54 (1994)).

The fractions from the Superdex-200 column that contained anti-HIV activity were pooled and analyzed by SDS-PAGE under reducing and non-reducing conditions and silver stain, which revealed a single molecular species migrating at a 43 kDa (FIG. 2B). In-gel trypsin digestion was performed on the material migrating at 43 kDa band to yield peptide fragments that were subsequently eluted from the gel and identified as bovine ATIII by reverse-phase HPLC nano-electrospray tandem mass spectrometry (μLC/MS/MS) on a Finnigan LCQ quadrupole ion trap mass spectrometer (FIG. 2C). Bovine ATIII (53%) was detected with masses of 14 peptides.

In contrast, serum containing untreated media and supernatants from unstimulated $CD8^+$ T-cell grown in serum containing serum did not substantially inhibit $HIV_{IIIB}$ replication, even when applied to the heparin Sepharose column. Additionally, using untreated serum containing media the 43 kDa form of ATIII was not detected following heparin Sepharose chromatography and Superdex200 chromatography by either SDS-PAGE silverstaining or C4-HPLC. These data show that activated $CD8^+$ T-cells modify ATIII into a form that is capable of inhibiting HIV. ATIII unprocessed normally has a molecular weight of 54-65 kDa, whereas the purified form was found at 43 kDa by SDS-PAGE. This led us to hypothesize that the heparin non-binding <50 kDa factor might be necessary to activate ATIII.

Example 2

Antiviral Activity of ATIII

1. Comparative Evaluation of the Effect of Purified Bovine ATIII Forms on HIV, SIV, and SHIV Infectivity In Vitro To test the effect of ATIII on lentivirus infectivity (X4 HIV, R5HIV, $SIV_{239}$ or $SHIV_{KU-1}$), cell lines (H9, PM1, SEM-174) were cultured in the presence or absence of the various forms of ATIII for up to nine days (Cf., FIGS. 3 and 4). Every three days (days 3, 6, and 9), 1 ml cell supernatant was removed from test wells and replaced with an equal volume of R20 culture medium containing either bovine ATIII or human ATIII. Control wells were similarly sampled, but received media without the ATIII supplement.

Both the test and the control wells were again sampled on the ninth day of culture and the concentration of the viral core protein p24 (gag) for the HIV (Alliance® HIV-1 p24 ELISA kit; NEN® Life Science, Boston, Mass., USA) or p27 antigen (SIV core antigen ELISA kit, Coulter, Miami, Fla.) was measured for HIV and SIV or SHIV infected cells, respectively Inhibition of viral replication in the test samples was calculated as a percentage of p24 immunoreactivity observed in control wells.

2. In Vivo Evaluation of ATIII Antiretroviral Activity.

Human cell lines can be cultivated in hollow fibers in the subcutaneous and intraperitoneal compartments of mice (Hollingshead et al., LIFE SCi., 57: 131-41 (1995)). In vivo evaluation of ATIII antiretroviral activity can be evaluated in the murine hollow fiber model developed by Hollingshead and coworkers (ANTIVIRAL REs., 28: 256-79 (1995)).

H9 or PM1 cell-bearing polyvinylidene fluoride fibers (500,000 Mw cutoff; 1 mm I.D.; Spectrum Medical Corp., Houston, Tex., USA) are prepared by filling conditioned hollow fibers with cell inoculum (uninfected cells, acutely HIV infected cells or chronically HIV infected cells) (Hollingshead et al., LIFE SCI., 57. 131-41 (1995)). These inoculated hollow fibers are surgically implanted either subcutaneously or in the peritoneal cavity of SCID mice (SCID/NCr; NCI Animal Production Facility, NCI-FCRDC, Frederick, Md., USA). Hollow-fiber-bearing SCID mice are dosed either acutely or chronically with increasing amounts of purified ATIII preparation. The ATIII preparation (3-500 U/mouse/day) are administered to the hollow-fiber-bearing SCID mice by subcutaneous injection, intraperitoneal injection, intravenous or oral routes. At select times, blood is sampled from control and test animals and serum prepared. The amount of viral particles in test and control serum is measured by p24 ELISA. ATIII-mediated antiviral action yield a significant decrease in viral load as judged by at least a 15% decrease in serum p24 protein content in ATIII-treated animals relative to the serum p24 content of the untreated control animals.

Example 3

Anti-Viral Activity of Modified ATIII

1. Viruses Tested

The NIH Biodefense program tested anti-viral activity of AB100 and AB200 (ATIII-heparin complex; i.e. modified ATIII) for the following viruses: HSV-1, HSV-2, Measles VEE, Tacarible Virus, SARS, Rift Valley Fever (MP-12), RSV A, Rhinovirus, PIV, FluA (H1N1, H3N2, H5N1, H1N1, H3N2, H5N1), Flu B, New Guinea virus, Adenovirus (65089, Chicago), WNV and Dengue (New Guinea C). Raymond Chung at Gastrointestinal Unit at the Massachusetts General Hospital tested HCV anti-viral activity. Anti-viral HIV activity was measured in the laboratory of Bruce Walker at the AIDS Research Center at the Massachusetts General Hospital.

2. Anti-Viral Activity

Anti-viral activities were found against HSV-1, HSV-2, HCV and HIV using modified ATIII. Using the CPE assay with HFF cells inhibition was found for the HSV-2 virus with a CC50 of 50 ug/ml. The SI was above factor 3125 and the ACV EC50 was 0.3. Modified ATIII had an EC50 of 3.57 pM for HSV-2. Here the EC90 was 5.36 pM, the CC50>890 nM (>50 μg/ml), a SI>250 with an ACV EC50 of 0.3. HCV anti-viral activity was measured in a replicon system with an EC50 of 4.2 μM (235 ug/ml). For HIV an EC50 of 84 nM was found where modified AT3 was given every 3 days and virus was measured at day 9.

3. Summary of Anti-Viral Tests Used Where Modified ATIII Showed Anti-Viral Activity 3.1 HSV-1/HSV-2 Test as Described at Website niaid-aacf.org/protocols/Herpes 3.1.1 Efficacy. In all the assays, a minimum of six drug concentrations was used covering a range of 100 pg/ml to 0.016 μg/ml, in 5-fold increments. These data allow to obtain good dose response curves. From these data, the dose that inhibited viral replication by 50% (effective concentration 50; $EC_{50}$) was calculated using the computer software program MacSynergy II by M. N. Prichard, K. R. Asaltine, and C. Shipman, Jr., University of Michigan, Ann Arbor, Mich.

3.1.2 Toxicity. The same drug concentrations used to determine efficacy were also used on uninfected cells in each assay to determine toxicity of each experimental compound. The drug concentration that is cytotoxic to cells as determined by their failure to take up a vital strain, neutral red, (cytotoxic concentration 50; $CC_{50}$) was determined as described above.

Since the greatest need for new drugs to treat herpes virus infections are for systemic diseases such as neonatal herpes, it is likely that these drugs will need to be given parenterally. It is very important therefore to determine the toxicity of new compounds on dividing cells at a very early stage of testing. A cell proliferation assay using HFF cells is a very sensitive assay for detecting drug toxicity to dividing cells and the drug concentration that inhibits cell growth by 50% ($IC_{50}$) was calculated as described above. In comparison with four human diploid cell lines and vero cells, HFF cells are the most sensitive and predictive of toxicity for bone marrow cells.

3.1.3 Assessment of Drug Activity. To determine if each compound has sufficient antiviral activity that exceeds its level of toxicity, a selectivity index (SI) was calculated according to $CC_{50}/EC_{50}$. A compound that had an SI of 10 or greater is considered to have anti-viral activity.

3.2 HCV test (i.e., replicon system) as described in Chung, R. T., W. He, A. Saquib, A. M. Contreras, R. J. Xavier, A. Chawla, T. C. Wang, and E. V. Schmidt. 2001. Hepatitis C virus replication is directly inhibited by IFN-alpha in a full-length binary expression system. Proc Natl Acad Sci USA 98:9847-9852.

For the HCV anti-viral test a replicon system was used. 0, 10, 50 and 250 μg/ml of modified ATIII was used in the test.

3.3.1.1 HIV test as described in Geiben-Lynn, R., M. Kursar, N. V. Brown, E. L. Kerr, A. D. Luster, and B. D. Walker. 2001. Noncytolytic inhibition of X4 virus by bulk CD8(+) cells from human immunodeficiency virus type 1 (HIV-1)-infected persons and HIV-1-specific cytotoxic T lymphocytes is not mediated by beta-chemokines. J Virol 75:8306-8316.

3.3.1 Assay for inhibition of HIV-$I_{IIIB}$ replication. H9 cells (HLA A1, B6, Bw62, Cw3) were acutely infected with at a multiplicity of infection of $10^2$ 50% tissue culture infective dose per ml and resuspended in R20. The cells were then plated in 2 ml R20 at $5\times10^5$ cells/ml in a 24-well plate. Modified ATIII concentrations were tested at 0, 10, 50, 250 μg/ml. H9 cell supernatant (1 ml) was removed every 3 days and replaced with medium supplemented with modified ATIII. After 9 days, the concentration of p24 was measured with an HIV-1 p24 enzyme-linked immunosorbent assay (ELISA) kit (NEM Life Science, Boston, Mass.), and the percentage inhibition was calculated against the medium control.

Example 4

Anti-Viral Activity of Activated ATIII

1. Viruses Tested

We tested antiviral activity of activated ATIII (ATIII after interaction with heparin, but not still bound, i.e., S-ATIII) for the following viruses: HSV-1, HSV-2, Measles VEE, Tacaribe Virus, SARS, Rift Valley Fever (MP-12), RSV A, Rhinovirus, PIV, FluA (H1N1, H3N2, H5N1, H1N1, H3N2, H5N1), Flu B, New Guinea virus, Adenovirus (65089, Chicago), WNV and Dengue (New Guinea C).

2. Anti-Viral Activity

Anti-viral activities were found against HSV-1 and HSV-2 using activated ATIII. Using the CPE assay with HFF cells strongest inhibition was found for the HSV-1 virus with an EC50 of <0.6 pM (<0.016 μg/ml), an EC90 of <0.6 pM. The CC50 was 50 pg/ml, the SI was above factor 3125 and the ACV EC50 was 0.3. Using the same assay activated ATIII had an EC50 of 3.57 pM for HSV-2. Here the EC90 was 5.36 pM, the CC50>890 nM (>50 μg/ml), a SI>250 with an ACV EC50 of 0.3.

3. Summary of Anti-Viral Tests Used Where Activated ATIII Showed Anti-Viral Activity 3.1 HSV-1/HSV-2 Test as Described at Website niaid-aacf.org/protocols/Herpes 3.1.1 Efficacy. In all the assays, a minimum of six drug concentrations was used covering a range of 100 pg/ml to 0.016 μg/ml, in 5-fold increments. These data allow to obtain good dose response curves. From these data, the dose that inhibited viral replication by 50% (effective concentration 50; $EC_{50}$) was calculated using the computer software program MacSynergy II by M. N. Prichard, K. R. Asaltine, and C. Shipman, Jr., University of Michigan, Ann Arbor, Mich.

3.1.2 Toxicity. The same drug concentrations used to determine efficacy were also used on uninfected cells in each assay to determine toxicity of each experimental compound. The drug concentration that is cytotoxic to cells as determined by their failure to take up a vital strain, neutral red, (cytotoxic concentration 50; $CC_{50}$) was determined as described above.

Since the greatest need for new drugs to treat herpes virus infections are for systemic diseases such as neonatal herpes, it is likely that these drugs will need to be given parenterally. It is very important therefore to determine the toxicity of new compounds on dividing cells at a very early stage of testing. A cell proliferation assay using HFF cells is a very sensitive assay for detecting drug toxicity to dividing cells and the drug concentration that inhibits cell growth by 50% ($IC_{50}$) was calculated as described above. In comparison with four human diploid cell lines and vero cells, HFF cells are the most sensitive and predictive of toxicity for bone marrow cells.

3.1.3 Assessment of Drug Activity. To determine if each compound has sufficient antiviral activity that exceeds its level of toxicity, a selectivity index (SI) was calculated according to $CC_{50}/EC_{50}$. A compound that had an SI of 10 or greater is considered to have anti-viral activity.

Example 5

Use of Serpin Drugs for Treatment of HIV/HCV Co-Transfections

Novel antivirals against HIV and HCV targeting host-cell proteins are needed to prevent the occurrence of multi-resistant viruses. The Serine protein inhibitors (Serpins) Secretory Leucocyte Protease Inhibitor (SLPI), anti-trypsin and Antithrombin III (ATIII) have potent antiviral activity against HIV in vitro. Their in vivo potential can be seen in the facts: a) the missing oral transmission most likely due to the anti-viral activity of SLPI, the predominant HIV-inhibitor in saliva; b) the correlation between disease progression and certain anti-trypsin mutations; c) the observation that $CD8^+$ T cell of HIV Long-term Non-progressors (patients infected for more than 10 years but show no signs of disease progression without anti-viral treatment) produce a modified form of ATIII with high anti-viral activities. ATIII is the first recombinant protein produced in goats and approved for human use. Due to its improved availability, 60 h half-life and low toxic profile ATIII offers new applications as an anti-viral against HIV and HCV.

HIV inhibition was measured in cell lines and human peripheral blood monocytes cells. HCV inhibition was measured using a replicon system. Activation or inhibition of pathways and host-cell target was measured by microarray with 84 key genes testing for 14 different pathways.

ATIII blocked HIV viral replication in nM and HCV in μM concentrations in a dose dependent manner. Using 2.4, 12 and 24 U/ml ATIII we saw 8 genes in HIV infected PBMC up-regulated (PTGS2, IL-8, IL-1α, CCL20, BCL2A1, MMP7, Fas and HK2). At the highest dose PTGS2 was up to 300 times, IL-8 up to 60 times and IL-1α up to 60 times up-regulated whereas PECAM1 and IL-2 were down-regulated, 7 and 3 times respectively. In the HCV replicon system seven genes were more than 10 times down-regulated. Cancer genes Jun and Myc were up to 1000 times and 80 times up-regulated, respectively, transcription factor CEBP was up-regulated more than 600 times.

Whereas HIV is possibly blocked due to up-regulation of proteins like the anti-inflammatory prostaglandins, HCV is down-regulated through proteins necessary for viral replication. ATIII blocks viral replication through an anti-viral mechanism of action which targets host-cell proteins which might diminish the ability of the viruses to gain resistance to the new treatment.

Example 6

ANTI-HLA-DR Immunoliposomes Encapsulating Serine Protease Inhibitors (Serpins) Targeting Virus-Infected Cells Current small molecule anti-HIV drugs are targeting viral structures in the replication cycle of HIV. Combinations of the various small-molecule drugs are used to delay the emergence of resistant viral variants, to increase potency and to broaden coverage against variants that exist in the population. Nevertheless, new antiretroviral drug regimens are needed, especially for subjects who have failed two or three previous regimens. Furthermore, to prevent further development of drug resistant HIV a new class of drugs is needed targeting host-cell proteins, which are necessary for the virus to replicate. These targets are less mutable, possibly making it more difficult for the virus to evolve resistance. In addition to the teachings herein, a number of recent clinical observations point to the possibility of the anti-inflammatory serine protease inhibitors (serpins) in controlling viral infections in the mucosa and the peripheral blood, possibly by blocking pathways necessary for HIV to replicate.

In this example antithrombin III (ATIII) was investigated as a prototypic member of this family of proteins as it displays up to $10^6$-fold higher in vitro anti-HIV activity than other serpins. HIV replicates only slowly in whole blood, but more rapidly in α1-antitrypsin deficient blood. Therefore, heparin activated ATIII (hep-ATIII) encapsulated in liposomes was used to target specifically the lymph nodes because the peripheral blood might already be saturated with serpins. Conventional liposomes were compared with sterically stabilized anti-HLA-DR immunoliposomes. Monocyte-derived macrophages, which are also $CD4^+$ and express HLA-DR, are the most frequent hosts of HIV-1 in tissues of infected individuals. Therefore, using HLA-DR antibodies engrafted into the surface of sterically stabilized liposomes were used for improved targeting.

For in vitro assays peripheral blood mononuclear cells (PBMCs) from HIV-1-seronegative donors were obtained by Ficoll-Hypaque density gradient centrifugation of heparinized venous blood. After 3-day mitogen stimulation, PBMCs were resuspended at a concentration of $1\times10^6$ cells/ml in RPMI 1640 culture medium (Sigma, St Louis, Mo.) supplemented with 10% fetal calf serum (Sigma), penicillin (50 U/ml), streptomycin (50 μg/ml), L-glutamine (2 mM), HEPES buffer (10 mM), and 50 U/ml interleukin-2 in 24-well tissue culture plates (Becton Dickinson, San Jose, Calif.). Conventional and sterically stabilized anti-HLA-DR liposomes encapsulating a heparin activated ATIII were added in serial dilutions at day 0 and day 4. HIV-1 inoculum (1,000 50% tissue culture infective doses/$10^6$ cells) was added to PBMC for 2 h at 37° C. and cells were washed extensively, afterwards liposome preparations were added in serial dilutions. Fifty percent of medium was replaced at day 4. Each condition was tested in triplicate. Cell-free culture supernatants were harvested and analyzed by an enzyme-linked immunosorbent assay (Du Pont, Wilmington, Del.) for HIV-1 p24 antigen production on day 7 of culture. In addition, uninfected drug-treated cytotoxicity controls were maintained at the highest concentration of each liposome tested. No toxicity was observed at highest concentrations tested, assessed by trypan blue dye exclusion method or Neutral Red staining.

Two clinical HIV-1 isolates, HIV-1 89.6 and SF162, were derived from PBMCs or cerebrospinal fluid of patients with AIDS, respectively. 89.6 replicates to high titers in primary human macrophages, primary human lymphocytes, CEMx174 and MT-2 cells. The HIV-1 isolate is syncytium-forming and highly cytopathic. It utilizes CCR5 and CXCR4 as co-receptors. Isolate SF162 is not easily neutralized by antibodies, does not grow in T- or U937 cells. SF120 utilizes CCR5 as a coreceptor.

Before encapsulation ATIII (Talecris, Durham, N.C.) was activated with heparin as previously described. The conventional liposomes for the studies were made as large liposomes through a mixture of phosphatidyl-choline and cholesterol, and were passed through 5 μm polycarbonate membrane filter to reach a final size of 1-2 μm. The sterically stabilized anti-HLA DR antibody (clone 2.06, $IgG_1$) immunoliposomes were produced as described earlier, with the modification that instead the Fab' fragment the whole antibody was used. The immunoliposomes had a final size of 100 nm. Per subcutaneous administration on day 0 and day 1 a delivery schedule of four equal depots of immunoliposomes (1.5 ml in total) were delivered close to the inguinal or axilliary lymph nodes. The animals used were chronically infected for more than 450 days with $SIV_{mac251}$ as previously described.

Two different liposome formulations encapsulating hep-ATIII were examined and their effects on viral replication in vitro were compared. Hep-ATIII encapsulated in sterically stabilized liposomes increased anti-viral activity 20-50 times compared to conventional liposomes (Table I) with $IC_{50}$ in a low nanomolar range. This indicates that the use of immunoliposomes increased the efficiency of delivery to the target cells.

Figure 12:
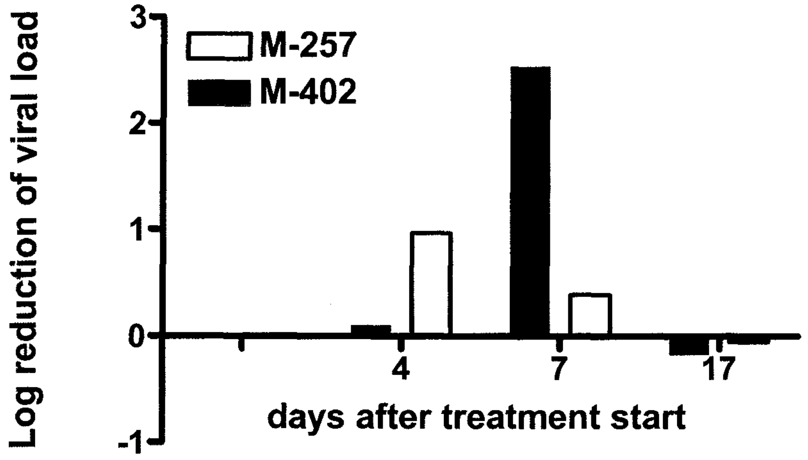
FIG. 12 is a bar graph showing the reduction of viral load in chronic infected rhesus macaques by sterically stabilized anti-HLA-DR immunoliposomes encapsulating hep-ATIII. Two Indian-origin macaques were chronically infected with $SIV_{mac251}$ for more than 450 days and then treated each via s.c. route with 4 depots of a total of 1.5 ml of 0.05 mg/ml hep-ATIII encapsulated in anti-HLA-DR immunoliposomes daily for two days.

The effect of the two different liposome formulations were then compared in in vivo experiments. Three animals treated with conventional liposomes (0.8 mg/ml hep-ATIII encapsulated) showed no effect on viral load. Animals treated with sterically stabilized anti-HLA DR antibody immunoliposome encapsulating 0.05 mg/ml hep-ATIII showed a 0.9-2.5 log reduction of viral load (FIG. 12). This confirms to the in vitro findings that the target cell specific delivery increased immunoliposomes efficiency.

As the microenvironment of lymphoid tissues is crucial for effective immune response, it is important to decrease viral burden and inhibit virus replication at the earliest possible time after infection. Three-drug treatment therapy markedly diminished the number of HIV-1 RNA copies found in the secondary lymphoid tissues such as the tonsils. However, a few copies of HIV-1 RNA were still detectable and could thus represent a focus of infection once the therapy is stopped due to the frequent toxicity seen in patients undergoing combined anti-retroviral therapy. As suboptimal concentrations of drugs within infected cells can potentially lead to the development of resistance, the delivery of high drug concentrations into HIV reservoirs could also reduce the frequency of resistance.

An immunoliposome formulation of the invention, can be used periodically to deplete residual viral reservoirs or used routinely in salvage patient populations, where resistant viruses prevail in spite of a multiple-drug treatment therapy. Rhesus macaque treatment: For non-human primate studies, two Indian-origin macaques were chronically infected with SIVmac251 for more than 450 days and then treated each via s.c. route with 4 inoculations of a total of 1.5 ml of 0.05 mg/ml hep-ATIII encapsulated in anti-HLA-DR immunoliposomes daily for two days. S.C. administrations were done in close proximity to the inguinal or axilliary lymph nodes.

TABLE 1

$IC_{50}$ of hep-ATIII encapsulated in different liposome formulations

| Formulation | Virus | $IC_{50}$ (nM) |
|---|---|---|
| Conventional | 89.6 | 24 |
| Liposome | SF162 | 22 |
| Anti-HLA-DR | 89.6 | 0.4 |
| Immunoliposome | SF162 | 0.7 |

Immunoliposome preparation: Step 1 is the derivation of antibody with NGPE: 0.6 ml of 0.1 M of octyl glucoside (OG) was added to 6 ml of MES/NaCl buffer. 3.30 mg of NGPE lipid (Sigma) was dissolved in 2 ml of chloroform and added to a 50 ml round bottom flask. The chloroform was dried in a rotary evaporator. The OG in MES buffer solution was added to the dried film. Then 1.1 ml of 0.25 M EDC (Sigma) was added to the solution. Afterwards, 1.1 ml of 0.1 M NHS was added and the solution was incubated at room temperature for 10 minutes. The pH was adjusted to 7.5. Fifty mg HLA-DR antibody (clone 2.06), which was dialyzed against a sodium borate buffer, was added. The solution was incubated for 12 hours at 4° C. and afterwards dialyzed against PBS buffer. The NGPE conjugated antibody was concentrated in a vacuum concentrator. Step 2: 40 mg of DOPA and 164 mg of DOPE (both Sigma) were dissolved in 100 ml of chloroform in a round bottom flask connected to a rotary evaporator. The chloroform was evaporated by vacuum until a thin lipid film was formed. The NGPE conjugated antibody and 1 ml hep-ATIII solution (20 mg/ml) was added to the dried lipid film. This film was hydrated overnight at 4° C. during to form the liposomes. The liposomes were sized to 100 nm by 20 times extrusion through a 5 micron polycarbonate membrane filter using a Lipex extruder. The liposomes were then dialyzed against 10 L of PBS buffer for 36 h.

Example 7

UP-Regulation and Down-Regulation of Gene Expression

Figure 13:
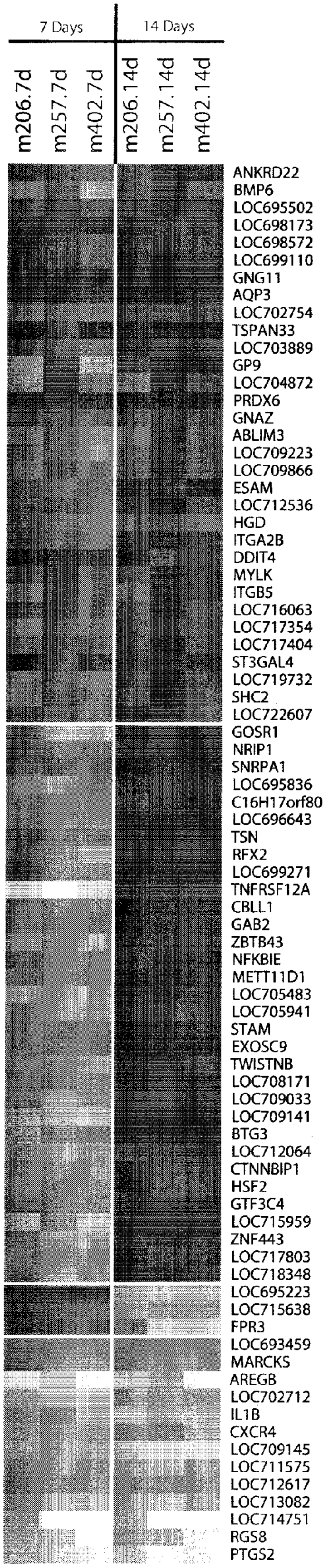
FIG. 13 is heat diagram of genes activated or down-regulated by heparin activated, hep-ATIII, and ATIII in three rhesus macaques.

FIG. 13 shows Target genes of Affymetrix gene expression profiling of genes activated after hep-ATIII and ATIII treatment. Heat diagram of genes activated or down-regulated by heparin activated, hep-ATIII, and ATIII is shown for three rhesus macaques. Software analysis was performed using the Ingenuity 4.0 software package. Only genes are shown which were significantly ($p<0.01$) altered at day 7 compared to same animals before treatment. For the analysis day 7 was used because here occurred the highest reduction of viral load. Fore ATIII treatment macaques were treated daily for 4 days with 50 mg/ml daily by intra-venous administration, then every other day for 14 days. PBMC were collected at day 14. For hep-ATIII treatment macaques were treated by intra-venous injection with 50 mg/ml once daily for 4 days. PBMC were isolated at day 7. Total RNA was purified from these PBMC after shredding cells using the QIAshredder homogenizer (Qiagen), which consists of a unique biopolymer-shredding system in a microcentrifuge spin-column format. Total RNA was purified using RNAeasy spin-columns (Qiagen) according to the manufacturer's protocol. Integrity and concentration of the RNA sample was tested using the Aglient BioAnalyser and readied for the Affymetrix system setup consisting of target preparation, target hybridization and fluidics station, probe array washing and staining, and probe array scan. Probe was analyzed by Ingenutity software.

Example 8

Use of Serpin Drugs for Treatment of H1N1 Viral Infection

Viral Inhibition Assay:

A. Visual or Visual-confirmation (Visual-CONF): Inhibition of Viral Cytopathic Effect (CPE) This test, run in 96 well flat-bottomed microplates, was used. In this CPE inhibition test, four log10 dilutions of ATIII (e.g. 1000, 100, 10, 1 μg/ml) were added to 3 cups containing the cell monolayer; within 5 min, the virus is then added and the plate sealed, incubated at 37° C. and CPE read microscopically when untreated infected controls develop a 3 to 4+ CPE (approximately after 72 to 120 hr). A known positive control drug is evaluated in parallel with test drugs in each test. This drug was ribavirin. Follow-up testing (Visual-CONF) was run in the same manner except 8 one-half log10 dilutions of ATIII was used in 4 cups containing the cell monolayer per dilution.

The data are expressed as 50% effective concentrations (EC50).

B. Neutral Red Assay: Increase in Neutral Red (NR) Dye Uptake

This test was run to validate the CPE inhibition seen in the initial test, and utilizes the same 96-well micro plates after the CPE has been read. Neutral red was added to the medium; cells not damaged by virus take up a greater amount of dye, which was read on a computerized micro plate autoreader. The method as described by McManus (Appl. Environment. Microbiol. 31:35-38, 1976) is used. An EC50 was determined from this dye uptake.

C. Virus Yield Assay

ATIII effect on reduction of virus yield was tested by assaying frozen and thawed eluates from each cup for virus titer by serial dilution onto monolayers of susceptible cells. Development of CPE in these cells is the indication of presence of infectious virus. As in the initial tests, a known active drug was run in parallel as a positive control. The 90% effective concentration (EC90), which is that test drug concentration that inhibits virus yield by 1 log10, is determined from these data.

TABLE 2

| Corp ID | Assay | Vehicle | Virus | Strain | Cell Line | Unit | Test Date | Trial | EC50 | EC90 | IC50 | SI |
|---|---|---|---|---|---|---|---|---|---|---|---|---|
| Antithrombin | Neutral Red | Company Buffer | Flu A (H1N1) | California/07/2009 | MDCK | µg/ml | Jun. 23, 2009 | 1 | 4.4 | | >100 | >23 |
| | Visual | Company Buffer | Flu A (H1N1) | California/07/2009 | MDCK | µg/ml | Jun. 23, 2009 | 1 | 1.8 | | >100 | >55 |
| | Virus Yield | Company Buffer | Flu A (H1N1) | California/07/2009 | MDCK | µg/ml | Jun. 30, 2009 | 2 | | 1.82 | | >55 |
| | Visual-CONF | Company Buffer | Flu A (H1N1) | California/07/2009 | MDCK | µg/ml | Jun. 30, 2009 | 2 | 1.8 | | >100 | >55 |

Table 2 shows data for MDCK cells infected with H1N1 virus and treated with the serpin, antithrombin, of the present invention. The dose that inhibited viral replication by 50% (90%) called inhibitory concentration 50, EC50 (EC90) was calculated using the MacSynergy II Software [98]. A screen for drug toxicity was conducted in parallel. To determine if each compound has sufficient antiviral activity that exceeds its level of toxicity, a therapeutic index (SI) was calculated according to EC50/IC50. A compound that had a SI of 10 or greater is considered to have high anti-viral activity.

Equivalents

Although particular embodiments have been disclosed herein in detail, this has been done by way of example for purposes of illustration only, and is not intended to be limiting with respect to the scope of the appended claims, which follow. In particular it is contemplated by the inventors that various substitutions, alterations, and modifications may be made to the invention without departing from the spirit and scope of the invention as defined by the claims. Other aspects, advantages, and modifications are within the scope of the invention. For example, ATIII can be used, for example, as an antiviral drug against other viruses (e.g., H1N1, HTLV-1, HTLV-2, HSV-1, HSV-2, EBV, HBV, HCV, or CMV).

What is claimed is:

1. A method of treating a human immunodeficiency virus (HIV) infection in a mammal comprising administering heparin-activated antithrombin III.

2. The method of claim 1, wherein said heparin-activated antithrombin III is encapsulated in liposomes.

3. The method of claim 2, wherein said liposomes are anti-HLA-DR immunoliposomes.

4. The method of claim 1, wherein said mammal is a primate.

5. The method of claim 4, wherein said primate is a human.

* * * * *